United States Patent
Groutas et al.

(10) Patent No.: US 6,420,401 B1
(45) Date of Patent: *Jul. 16, 2002

(54) 1,2,5, THIADIAZOLIDIN-3-ONE 1,1-DIOXIDE DERIVATIVES

(75) Inventors: William C. Groutas; Rongze Kuang, both of Wichita, KS (US)

(73) Assignee: Wichita State University, Wichita, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/916,693

(22) Filed: Aug. 22, 1997

(51) Int. Cl.$^7$ .................. A61K 31/41; A61K 31/35; C07D 285/10

(52) U.S. Cl. .................. 514/362; 514/372; 514/456; 514/457; 514/382; 514/381; 514/345; 549/250; 549/252; 549/289

(58) Field of Search .................. 514/456, 459, 514/382, 381, 345, 362, 372; 549/250, 252, 289; 548/135

(56) References Cited

U.S. PATENT DOCUMENTS

| | | | |
|---|---|---|---|
| 4,785,010 A | 11/1988 | Zoller et al. | 514/356 |
| 5,128,339 A | 7/1992 | Dunlap et al. | 514/253 |
| 5,236,917 A | 8/1993 | Dunlap et al. | 514/338 |
| 5,250,696 A | 10/1993 | Dunlap et al. | 548/210 |
| 5,296,496 A | 3/1994 | Desai et al. | 514/373 |
| 5,306,818 A | 4/1994 | Subramanyam et al. | 544/135 |
| 5,494,925 A | 2/1996 | Court et al. | 514/362 |
| 5,512,576 A | 4/1996 | Desai et al. | 514/258 |
| 5,541,168 A | 7/1996 | Court et al. | 514/92 |
| 5,550,139 A * | 8/1996 | Groutas | |
| 5,556,909 A | 9/1996 | Desai | 514/362 |
| 5,602,154 A | 2/1997 | Desai | 514/342 |

FOREIGN PATENT DOCUMENTS

| | | | |
|---|---|---|---|
| WO | WO 95/18797 | 7/1995 | C07D/285/10 |
| WO | WO 96/16649 | 6/1996 | A61K/31/41 |
| WO | WO 96/16654 | 6/1996 | A61K/31/44 |
| WO | WO 96/16951 | 6/1996 | C07D/285/10 |
| WO | WO 96/16952 | 6/1996 | C07D/285/10 |
| WO | WO 96/16970 | 6/1996 | C07F/9/09 |
| WO | WO 97/27180 | 7/1997 | C07D/233/36 |

OTHER PUBLICATIONS

Groutas et al. "Substituted 3–oxo–1,2,5–thiadiazolidine 1,1–Dioxide" Biochemical and Biophysical Research Communications 198: 341–349, 1994.*

Aouf, N. et al., "Synthese et Cyclisation de Carboxysulfamides Derives D'Aminoacides," Tetrahedron Letters 32:6545–6546, 1991. (English abstract).

Dewynter, G. et al., "Synthése de 'sulfahydantoïnes' chirales. Aspects stéréochimiques et protection régiospécifique," Tetrahedron 49:65–76, 1993. (English abstract).

Groutas, W., "Mechanism–Based Inhibitors of Serine Proteinases," Grant–Application to the Department of Health and Human Services, Public Health Service, 61 pages, 1997.

Groutas, W.C. et al., "Structure–Based Design of a General Class of Mechanism–Based Inhibitors of the Serine Proteinases Employing a Novel Amino Acid–Derived Heterocyclic Scaffold," Biochemistry 36:4739–4750, 1997.

(List continued on next page.)

Primary Examiner—Floyd D. Higel
Assistant Examiner—Ebenezer Sackey
(74) Attorney, Agent, or Firm—David J. Weitz; Wilson Sonsini; Goodrich & Rosati

(57) ABSTRACT

Substituted derivatives of 1,2,5-thiadiazolidin-3-one 1,1-dioxides, oligomers containing them, and methods of using them.

36 Claims, 2 Drawing Sheets

OTHER PUBLICATIONS

Groutas, W.C. et al., Structure–Based Design of Amino Acid–Derived Heterocyclic Mechanism–Based Inhibitors of Serine Proteinases, "A Abstract for Protease Inhibitors in Infectious Diseases" and "Protease Inhibitors in Inflammation" Conferences, San Diego, CA, Feb. 10–12 1997.

Groutas, W.C.et al., "A Novel and General Class of Heterocyclic Mechanism–Based Inhibitors of Serine Proteinases," Abstract for "Protease Inhibitors: New Therapeutics and Approaches" Conference, Baltimore, MD, Nov. 6–7, 1996.

Groutas, W.C. et al., "Substituted 3–Oxo–1,2,5–thiadiazolidine 1,1–Dioxides: A New Class of Potential Mechanism–Based Inhibitors of Human Leukocyte Elastase and Cathepsin G," Biochemical and Biophysical Research Communications, 198:341–349, 1994.

Günther, D. and Soldan, F., "Radikalinduzierte Reaktionen von Olefinen mit Chlorsulfonylisocyanat," Chem. Ber. 103:663–669, 1970. (English abstract).

Hanewacker, G.–A. et al., "New 2,4,4–Trisubstituted 3–Oxo–1,2,5–thiadiazolidine 1,1–Dioxides," Arch. Pharm. (Weinheim) 326:497–498, 1993. (English title).

Lee, C.–H. And Kohn, H., "Anticonvulsant Properties of 3–Oxo– and 3–Imino–4–Substituted 1,2,5–Thiadiazolidine 1,1–Dioxides," Journal of Pharmaceutical Sciences 79:716–718, 1990.

Lee, C.–H. et al., "3–Oxo– and 3–Imino–4–substituted–1, 2,5–thiadiazolidine 1,1–Dioxides: Synthesis, Spectral Properties, and Selected Chemistry," J. Org. Chem. 54:3077–3083, 1989.

Muller, G.W. and DuBois, G.E., "A General Synthesis of 4–Substituted 1,1–Dioxo–1,2,5–thiadiazolidin–3–ones Derived from α–Amino Acids," J. Org. Chem. 54:4471–4473, 1989.

Unterhalt, B. and Hanewacker G.–A., "2,4–Disubstituierte 3–Oxo–1,2,5–thiadiazolidin–1,1–dioxide," Arch. Pharm. (Weinheim) 321:375–376, 1988. (English Title).

Unterhalt, B. and Hanewacker G.–A., "Synthese sulfonylanaloger Hydantoine," Arch. Pharm. (Weinheim) 321:749–751, 1988. (English Abstract).

Groutas, W.C., et al., "Structure–Based Design of a General Class of Mechanism–Based Inhibitors of the Serine Proteinases Employing a Novel Amino Acid–Derived Heterocyclic Scaffold", *Biochemisty*, Feb. 10, 1997, vol. 36, No. 16, pp. 4739–4750.

Groutas, W.C., et al., "Substituted 3–OXO–1,2,5–Thiadiazolidine 1,1–Dioxides: A New Class of Potential Mechanism–Based Inhibitors of Human Leukocyte Elastase and Cathespin G", *Biochemical and Biophysical Research Communications*, Jan. 14, 1994, vol. 198, No. 1, pp. 341–349.

Kuang, R., et al., "Use of the 1,2,5–Thiadiazolidin–3–One 1,1 Dioxide and Isothiazolidin–3–One 1,1 Dioxide Scaffolds in the Design of Potent Inhibitors of Serine Proteinases", *Bioorganic & Medicinal Chemistry Letters*, Jan. 26, 1998, vol. 8, pp. 539–544.

Lee, C.H., et al., "3–Oxo and 3–Imino–4–substituted–1,2, 5–thiadiazolidine 1,1–Dioxides: Synthesis, Spectral Properties, and Selected Chemistry", *J. Org. Chem.*, Jan. 24, 1989, vol. 54, No. 13, pp. 3077–3083.

Groutas, W.C., et al., "Potent and Specific Inhibition of human Leukocyte Elastase, Cathepsin G and Proteinase 3 by Sulfone Derivatives Employing the 1,2, 5–Thiadiazolidin–3–one 1,1 Dioxide Scaffold", *Bioorganic & Medicinal Chemistry*, Oct. 30, 1998, vol. 6, pp. 661–671.

* cited by examiner

1,2,5, THIADIAZOLIDIN-3-ONE 1,1-DIOXIDE DERIVATIVES

STATEMENT AS TO FEDERALLY SPONSORED RESEARCH

This application was Federally sponsored in part by NIH Grant No. 308048. As a result, the U.S. government may have rights to some part of the invention described herein.

BACKGROUND OF THE INVENTION

The invention relates to peptidomimetics which are substituted derivatives of 1,2,5 thiadiazolidin-3-one-1,1-dioxide.

Degenerative diseases associated with serine proteases such as human leukocyte elastase include cystic fibrosis, chronic obstructive pulmonary disease (e.g., emphysema and asthma), adult respiratory distress syndrome (ARDS), inflammatory bowel disease, chronic bronchitis, psoriasis, rheumatoid arthritis, pancreatitis, periodontal disease, and other inflammatory diseases.

Diseases associated with cysteine proteases include cancer metastasis, osteoporosis and osteoarthritis (McGrath et al. (1997) *Nature: Structural Biology* 4(2):105–109), bone resorption, muscular dystrophy, parasitic diseases (leishmaniasis, malaria) (Li et al. (1996) *Bioorg. Med. Chem.* 4(9):1421–1427; Rosenthal et al. (1993) *J. Clin. Invest.* 91:1052–1056), inflammation, common cold (Webber et al. (1996) *J. Med. Chem.* 39:5072–5082), and hepatitis A (Malcolm et al. (1996) *Biochemistry* 34:8172–8179).

SUMMARY OF THE INVENTION

The invention features a compound having the formula (I)

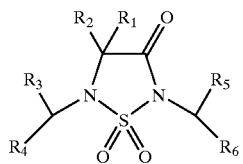

(I)

Each of $R_1$ and $R_3$, is independently selected from H, alkyl, aryl, aralkyl, alkaryl, and substituted aryl. $R_5$ is selected from the values for $R_1$ and halo. $R_2$ is selected from H, alkyl, aralkyl, alkylthioalkyl, hydroxyalkyl, and $R_{xxi}$ (amino acids). $R_4$ is H, alkyl, aryl, aralkyl, an amino acid side chain, —PO(OR$_A$)$_2$, —N=C=O, —(NHCHR$_i$CO)OR$_C$, —NHCOOR$_C$, —NHCONR$_X$R$_Y$, —(C=O)—Q, —CH(R$_i$)NHW, —[CHR$_{i(r)}$NH(C=O)]$_r$R$_C$, —[CHR$_{i(r)}$(C=O)NH]$_r$R$_C$ or —NHG. Q is —OR$_C$, —OJ, NR$_Y$R$_Z$, a halogen, —[NHCHR$_{i(q)}$(C=O)]$_q$OR$_C$, —[NHCHR$_{i(q)}$(C=O)]$_q$NR$_C$R$_E$, —OPn, or —NHPn. Pn is a polymer; each of W and W$^1$ is H, G, or —(C=O)NHCHR$_i$COOR$_C$. Each of q and r is an integer between 1 and 10. $R_6$ is selected from H, alkyl, aryl, aralkyl, —N=C=O, —(C=O)R$_B$, —(C=O)Q', —(NHCHR$_{xi}$(C=O))OR$_D$, —NH$_2$, —NHG, —NHCOOR$_D$, —NH(C=O)NR$_K$R$_L$, —O(C=O)CH$_2$—(OCH$_2$CH$_2$)$_2$—OR, and —O—X. R is alkyl. Q' is —OR$_D$, —OJ, —NR$_K$R$_L$, —[NHCHR$_{xi(z)}$(C=O)]$_z$—OR$_D$, or a halogen. X is —(C=O)R$_B$, —[(C=O)CH(R$_{xi(z)}$)—NH]$_z$X$_p$, —CH(R$_{xi}$)NHY, —CHR$_{xi}$(NH(C=O)CHR$_{xi(p)}$)$_p$—NHW$^1$, —[(C=O)NHCHR$_{xi(z)}$]$_z$—(C=O)OR$_D$, —(C=O)OR$_D$, —S(O)$_n$R$_B$, or —N(SO$_2$R$_Q$)—[(C=O)K]. $X_p$ is H or G, G being an amino protecting group. J is a carboxyl protecting group. Y is H, R$_B$, —(C=O)R$_B$, or G; z is between 1 and 10, n is from 0 to 2. K is R$_B$, —OR$_B$, —NHR$_B$, —OCHR$_{xi}$NHV, —[NHCHR$_{xi(m)}$(C=O)]$_m$OR$_B$, or —[NHCHR$_{xi(m)}$(C=O)]$_m$NR$_C$R$_F$. V is G, H, or —(C=O)CHR$_{xi}$NHZ. Z is G or H; m is from 1 to 2. In addition, $R_5$ and $R_6$ can be taken together to form a lactone. Each of $R_i$ through $R_{xxi}$ is independently selected from an amino acid side chain. Each of $R_A$ and $R_B$ is independently selected from alkyl, aryl, aralkyl, alkaryl, and heterocyclic radical. Each of $R_C$ and $R_D$ is independently selected from H and the values for $R_A$. Each of $R_E$ and $R_F$ is independently selected from (heterocyclic radical) alkyl. Each of $R_Y$ and $R_Z$, and each of $R_K$ and $R_L$, is independently selected from the values for $R_C$. Furthermore, each pair ($R_Y$ and $R_Z$, or $R_K$ and $R_L$) can be taken together to form a bivalent moiety selected from alkylene, heterocyclic diradical, alkenylene, arylene, or alkylarylene. $R_Q$ is selected from the values of $R_A$ and NHR$_r$. $R_r$ is alkyl, aryl, or aralkyl, provided that where one of $R_5$ and $R_6$ is H and the other is benzyl, and one of $R_3$ and $R_4$ is H, the other of $R_3$ aand $R_4$ is not alkyl; and provided that where one $R_3$ and $R_4$ is H, and the other is alkyl, and one of $R_5$ and $R_6$ is H, the other $R_5$ and $R_6$ is not —O(C=O)-aryl. The invention also features oligomers and polymers containing one or more of the disclosed inhibitor compounds.

The invention also features oligomers and polymers containing one or more of the disclosed inhibitor compounds. One embodiment is a peptidomimetic composition including between 1 and 20 monomers of a compound of formula (II); and between 0 and 19 amino acid residues. The monomers and amino acid residues are linked to each other by amide linkages, and the terminal monomers or amino acid residues are terminated by hydroxyl, amino, —OJ, or —NHG to form carboxyl, primary amide, or protected amino or carboxyl groups. For example, a terminal monomer may have a HO—[(C=O)— or a H[NH— terminus, where the bracket is the bracket in formula II. Formula II is shown below.

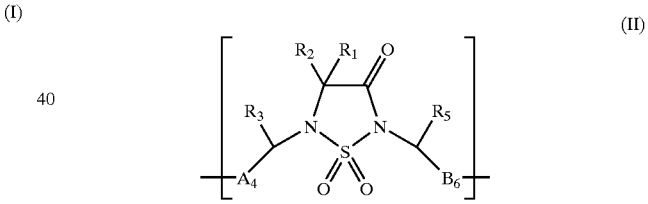

(II)

In formula II, $A_4$ is selected from —[NHCH(R$_i$)—, —[(C=O)—, and —[NH—. $B_6$ is selected from —CH(R$_i$)NH]—, —NH]— and —(C=O)]—. Each of $R_1$ and $R_3$ is independently selected from the H, alkyl, aryl, aralkyl, alkaryl, and substituted aryl. $R_5$ is selected from the values for $R_1$ and halo. $R_2$ is selected from H, alkyl, aralkyl, alkylthioalkyl, hydroxyalkyl, and an amino acid side chain. G is an amino protecting group. J is a carboxyl protecting group. Each $R_i$ is independently selected from an amino acid side chain. In some embodiments, the sum of the number of monomers and the number of amino acid residues is between 4 and 10, or between 2 and 6. In other embodiments, the number of monomer units is preferably between 2 and 8; the number of amino acid residues is 0, or between 0 and 6; at least two of the monomer units are the same; at least two of the monomer units are different; two of the monomer units have different $R_1$ groups; or combinations thereof.

Another aspect of the invention features a method for synthesizing a peptidomimetic product. The method includes covalently linking a compound of formula I to an amino acid residue or a peptidomimetic reactant having an isocyanate, chloroformate, hydroxyl, or preferably amino, activated amino, carboxyl, or activated carboxyl functional group. The resulting linking moiety is selected from urea, urethane, ester, and preferably amide linkages.

The invention also features a method of N-chloromethylating a cyclic N-acylated sulfamide, or the sulfonamide analog, including reacting a compound of formula III:

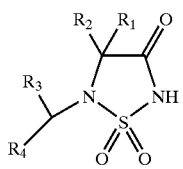
(III)

with at least 2 equivalents of a bisulfite adduct of formaldehyde in thionyl chloride at a temperature between 50° C.–120° C. for a reaction time between 2–30 hours. In formula III each of $R_1$ and $R_3$ is independently selected from H, alkyl, aryl, aralkyl, alkaryl, and substituted aryl. $R_2$ is selected from H, alkyl, aralkyl, alkylthioalkyl, hydroxyalkyl, and $R_{xxi}$. $R_4$ is H, alkyl, aryl, aralkyl, an amino acid side chain, —PO(OR$_A$)$_2$, —N=C=O, —(NHCHR$_i$CO)OR$_C$, —NHCOOR$_C$, —NHCONR$_X$R$_Y$, —(C=O)—Q, —CH(R$_i$)NHW, —[CHR$_{i(r)}$NH(C=O)]$_r$R$_C$, —[CHR$_{i(r)}$(C=O)NH]$_r$R$_C$, or —NHG. Q is —OR$_C$, —OJ, —NR$_Y$R$_Z$, a halogen, —[NHCHR$_{i(q)}$(C=O)]$_q$OR$_C$, —[NHCHR$_{i(q)}$(C=O)]$_q$NR$_C$R$_E$, —OPn, or —NHPn. Pn is a polymer, each of W and W$^1$ is H, G, or —(C=O)NHCHR$_i$COOR$_C$, and each of q and r is an integer between 1 and 10. Each of R$_i$ through Rxxi is independently selected from an amino acid side chain. R$_A$, R$_C$, R$_E$, R$_Y$ and R$_Z$ are as in formula I. In some embodiments, the amount of bisulfite adduct is at least 3 equivalents, between 5 and 10 equivalents, or between 4 and 8 equivalents. In another embodiment, R$_4$ and R$_6$ of formula III are not selected from reactive functional groups such as carboxyl, primary and secondary amines, amino, aldehyde, and primary amides. For example, R$_4$ is H, alkyl, aryl, aralkyl, an amino acid side chain, —PO(OR$_A$)$_2$, —(NHCHR$_i$CO)OR$_C$, —NHCOOR$_C$, —NHCONR$_X$R$_Y$, —(C=O)—Q, —CH(R$_i$)NHW, —[CHR$_{i(r)}$NH(C=O)]$_r$R$_C$, —[CHR$_{i(r)}$(C=O)NH]$_r$R$_C$, or —NHG, where Q is —OR$_C$, —OJ, —NR$_Y$R$_Z$, a halogen, —[NHCHR$_{i(q)}$(C=O)]$_q$OR$_C$, —[NHCHR$_{i(q)}$(C=O)]$_q$NR$_C$R$_E$, —OPn, or —NHPn, provided each of R$_C$, R$_X$, and R$_Y$ is not hydrogen.

The disclosed inhibitors are useful in methods of treating a protease-related condition, such as a degenerative disease, wherein a pharmaceutically effective amount of a composition including one or more disclosed inhibitors is administered to a patient. The invention also features synthetic chemical methods of making the disclosed compounds, including synthetic intermediates.

Other features and advantages of the invention will be apparent from the detailed description and examples below.

DETAILED DESCRIPTION OF THE INVENTION

Figure 1:
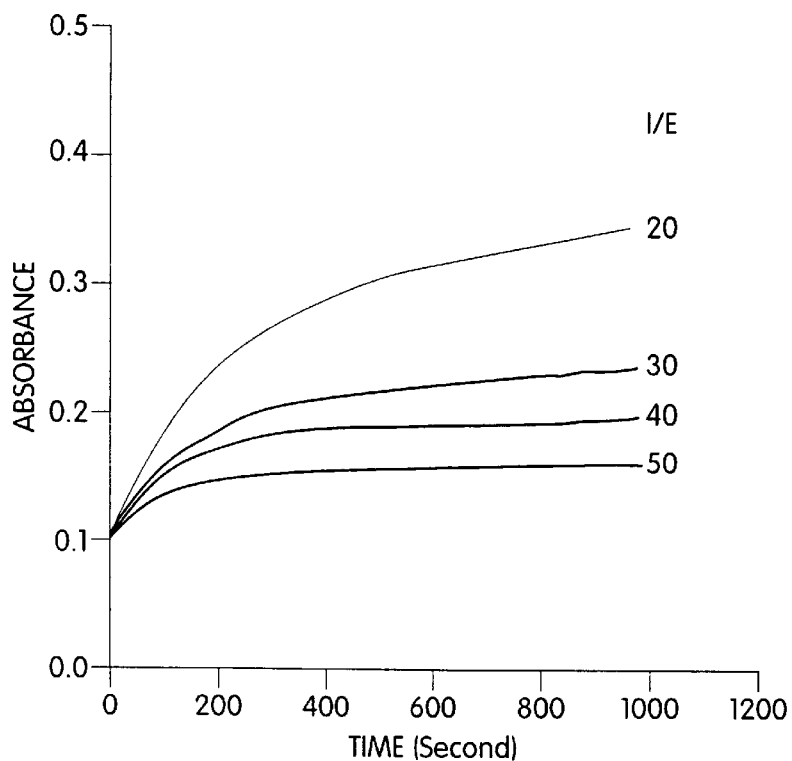
FIG. 1 shows an absorbance progress curve for the inhibition of human leukocyte elastase (HLE) by compound 42 (Table 2). Absorbance was recorded at 410 nm for reaction solutions containing 20.0 nM HLE, 1.00 mM MeOSuc-Ala-Ala-Pro-Val p-nitroanilide, and the indicated concentrations of inhibitor in 0.1 M HEPES buffer, pH 7.25, and 3.6% dimethyl sulfoxide. The temperature was maintained at 25° C., and the reactions were initiated by the addition of enzyme.

The invention features a universal template for creating biologically active, peptidomimetic compounds, such as those of formula I above. The chemical stability, side chain orientation, and polarity characteristic of the disclosed core template combine to provide numerous inhibitors of a variety of enzymes, including serine and cysteine proteases and proteasome. The disclosed compounds are designed to have inhibitory activity, including selectivity and improved subsite interactions, by varying the side chains, such as $R_1$, $R_4$ or $R_6$ or combinations thereof.

Based on formula I, some embodiments include a compound wherein (a) $R_4$ is terminated by carboxyl, acid halide, or amino; (b) $R_6$ is terminated by carboxyl or amino; or (c) $R_4$ is terminated by carboxyl, acid halide, or amino, and $R_6$ is terminated by carboxyl or amino. Another embodiment includes a compound wherein W is G or —(C=O)NHCR$_{xi}$(C=O)OR$_A$, and R$_C$ and R$_D$ are independently selected from the values of R$_A$, and at least one of R$_Y$ and R$_Z$, and at least one of R$_K$ and R$_L$, is independently selected from R$_A$; and X$_p$ is independently selected from the values of G, Y is R$_B$, —(C=O)—R$_B$, or independently selected from the values of G, V is independently selected from the values of G or —(C=O)CHR$_{xi}$NHZ, and Z is independently selected from the values of G. One embodiment includes a compound wherein R$_4$ is terminated by carboxyl, acid halide, or amino; wherein R$_6$ is terminated by carboxyl or amino; wherein R$_4$ and R$_6$ are each carboxyl or are each amino; wherein at least one of q and r is between 1 and 6, between 1 and 5, between 2 and 4, or between 4 and 6; wherein at least one of q and r is at least 3 (e.g., q is between 4 and 6 and r is between 1 and 5); wherein R$_2$ is selected from alkylacyloxyalkyl, arylalkyloxyalkyl, and protected amino acid side chains; wherein the halogen is selected from F and Cl; or wherein R$_{i(2)}$ is Pro, R$_{i(3)}$ is Ala, or R$_{i(4)}$ is Ala; or a combination thereof. Examples include R$_{i(1)}$-Pro-Ala-Ala, R$_{i(1)}$-Pro-R$_{i(3)}$-Ala, R$_{i(1)}$-R$_{i(2)}$-Ala-R$_{i(4)}$, and R$_{i(1)}$-Pro-Ala-R$_{i(4)}$.

The invention also features a compound wherein R$_{i(1)}$ is selected from Val, Leu, Norval, Norleu, Abu, and Phe; wherein R$_{xi(11)}$, R$_{xi(12)}$, and R$_{xi(13)}$ are hydrophobic; or wherein at least two (or at least three, or at least four, or at least five) of R$_1$, R$_2$, R$_3$, R$_4$, R$_5$, and R$_6$ are not H; or a combination thereof. For example, the "at least two of R$_1$ to R$_6$" can include R$_1$ and R$_2$; R$_3$ and R$_5$; R$_6$ and R$_4$;R$_5$ and R$_1$; or R$_3$, R$_4$, and R$_6$. In other words, each of R$_4$ and R$_6$ is not H; in some cases, each of R$_4$ and R$_6$ is not H and at least one of the remaining R$_1$, R$_2$, R$_3$, and R$_5$ is not H. Embodiments also include a compound wherein at least one of each pair (selected from R$_1$ and R$_2$, R$_3$ and R$_4$, and R$_5$ and R$_6$) has a fragment formula weight less than 150, or between 10 and 150, or between 75 and 150. For example, the fragment formula weight of methyl is 15 and the fragment formula weight of hydroxymethyl is 31.

The invention also features a compound, wherein $R_4$ is selected from —CO—Q; wherein Q is $NR_YR_Z$ or —[NHCHR$_{i(q)}$(C=O)]$_q$OR$_C$; wherein q is between 1 and 6; wherein Q is a halogen; wherein $R_6$ is selected from (C=O)—Q'; wherein Q' is OR$_B$, NR$_KR_L$, or —[NHCHR$_{xi}$(z)(C=O)]$_z$OR$_D$; wherein Q' is a halogen; wherein $R_4$ and $R_6$ are the same; and wherein $R_6$ is —N(SO$_2$R$_Q$)—[(C=O)K]. In some preferred embodiments, $R_{xi(z)}$ is phenyl, and $R_D$ is methyl or H.

According to another aspect of the invention, polymers, copolymers, and block copolymers can be constructed from one or more disclosed compounds (e.g., formula I). Each disclosed compound can be considered a monomeric unit, which can be linked in turn directly to another monomer of formula I, for example, or to an amino acid residue (e.g., by an amide or ester linkage), or mixed with other disclosed compounds in repeating (—[AB]—, or —[ABC]—), non-repeating ([ABCDEFGH] or [AABCAADEAA]) or block copolymers (—[A][B][A]— or —[A][BC]—). There may be between 2 and 50 units (and preferably between 2 and 20, e.g., 2–15, 4–10, or 2–5) selected from disclosed inhibitor monomers, amino acids, and biocompatible polymers. These may also be combined with other biocompatible spacers or copolymers. A spacer may be an alkylene group, a structure-determining group (e.g., a beta-turn mimic, an isostere for a peptide bond or other spatially constrained group), or a solubility-enhancing group (hydrophobic, hydrophilic, polar, polar aprotic, or nonpolar group).

Where $R_4$ and $R_6$ are amino- or carboxyl-terminated, an inhibitor monomer can be used in a manner analogous to a natural or non-natural amino acid to synthesize peptidomimetics according to standard automated or synthetic procedures. For example, where $R_4$ and $R_6$ are both carboxyl-terminated, protection of one of $R_4$ and & with t-butyl and the other with benzyl allows selective elaboration of each carboxyl group. Similarly, standard Boc and Cbz chemistry is used where $R_4$ and $R_6$ are both amino-terminated, the former being removed by TFA and the latter being removed by catalytic hydrogenation. Where $R_4$ and $R_6$ are the same in a given inhibitor monomer, the C-terminal to N-terminal orientation is discontinuous. In other words, the molecule may be, from left to right, N-terminal to C-terminal until the inhibitor monomer is reached ($R_4$) then (continuing to the right from $R_6$) the molecule is C-terminal to N-terminal. This separation and reverse C-/N-terminal orientation can allow inhibition of two or more enzymes oriented diagonally across the molecule using an oligomer of overall smaller molecular weight, since the discontinuity provides more space between the enzymes, relative to a repeated sequence along the same length and side. The reverse C-/N-terminal orientation, and the length of the peptide or peptidomimetic sequences attached to $R_4$ and $R_6$ can also bring two or more enzymes or receptors in proximity to each other in a desired conformation to promote further interaction. The sequences attached to $R_4$ and $R_6$ may interact with each other to form a secondary or tertiary structure that enhances the activity of one or more inhibitor monomers, e.g., by mimicking subsites or other local protein structure environments. Disclosed compounds, or oligomers containing them, can also be used to inhibit protein folding, e.g., aggregation of tetrameric or dimeric proteins.

These inhibitor polymers or oligomers can be formed using combinatorial or matrix techniques and subsequently assayed for biological activity, including inhibition of enzymes. A plurality of different inhibitor monomers in a disclosed polymer provides multiple pharmacological activities, e.g., a single composition which inhibits multiple serine proteases, a proteasome, or other enzymes, with varying specificity. As with the monomeric units, specificity is controlled in part by the selection of R groups (e.g., $R_3$, $R_4$, $R_6$, and particularly $R_1$). The tertiary and quaternary structures of such inhibitor polymers can result in a multi-active oligomer which presents active recognition and inhibitor sites on different facets of the oligomer under physiological conditions. The pharmacokinetic and pharmacodynamic properties include high metabolic stability and oral activity, as well as the ability to bind to or to activate a receptor, or to inhibit an enzyme. Metabolic stability is provided by selecting metabolism-resistant spacer groups or other linkages, e.g., replacing an amide bond with an $sp^2$ hydrocarbon configuration. The inhibitor polymers or peptidomimetics can be terminated with —(C=O)—Q' or —(C=O)R$_i$ in the N-terminii and Q on the C-terminii. Examples include the following structures.

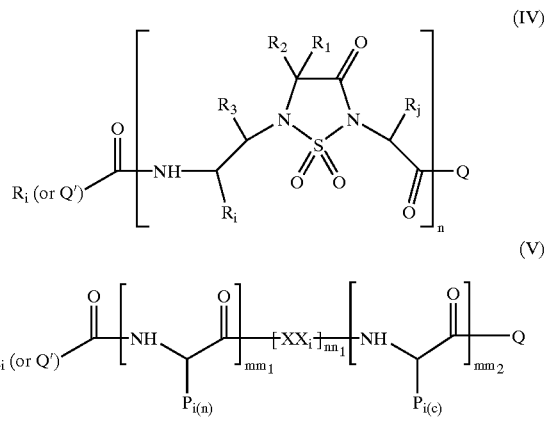

wherein $XX_i$ is

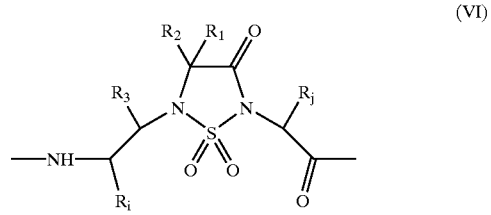

For example, an oligomer which contains one $XX_i$ in which $R_1$=isobutyl, =$R_2$H, and $R_3$, $R_5$, and $R_i$=H or $C_{1-4}$akyl may inihibit HLE. Similarly, where $R_i$=—(CH$_2$)$_4$—NH$_2$, $R_2$=H, and $R_3$, $R_5$, and $R_i$=H or $C_{1-4}$alkyl, the oligomer may inhibit trypsin and trypsin-like serine proteases. The potency of the oligomer is enhanced by selecting mm$_1$ and mm$_2$ amino acid residues $P_{i(n)}$ and $P_{i(c)}$ based on the known subsite specificity of the target enzyme. Another example is a molecule of formula I wherein $R_4$ is —CHR$_i$NH$_2$ and $R_6$ is COOH, i.e., a non-natural amino acid which can be incorporated into a peptide or peptidomimetic (or libraries thereof) by combinatorial or standard synthetic methodology. Other compositions of formula I are suitable, such as those wherein: $R_4$ is amino and $R_6$ is carboxyl; $R_4$ is carboxyl or protected carboxyl and $R_6$ is amino or protected amino; $R_4$ is carboxyl or protected carboxyl, and $R_6$ is —CH(R$_i$)NHW where W is H or G; each of $R_4$ and $R_6$ is carboxyl or protected carboxyl; each of $R_4$ and $R_6$ is amino or protected amino; and each of $R_4$ and $R_6$ is —CH($R_i$)NHW. The sum of variable $mm_1$, $nn_1$, and $mm_2$ is generally between 2 and 50, and preferably between 2 and 10 or 4 and 12. Side chains $P_{i(n)}$ and $P_{i(c)}$ are natural or non-natural amino acid side chains, as described herein. Each $XX_i$ is independently selected from the compounds disclosed in formula I with appropriate deletions at the C- and N-termini to form linkages (shown above as amide bonds, but also including ester, ether, urea, urethane, and unsaturated C—C linkages) to the peptide sequences or peptidomimetic sequences [NHP$_{i(n)}$CO] and [NHP$_{i(c)}$CO]. Where the linkage between the $XX_i$ moiety and the adjacent peptide or peptidomimetic sequence is not an amide linkage, the terminal carbonyl and —NH— groups are replaced by the selected linkage. The remaining groups $R_1$–$R_5$ are as in formula I.

The invention features some compounds which have two or more amino acid residues linked by amide bonds, e.g., [NHCHR$_{i(q)}$CO]$_q$ or [(C=O)NHCHR$_{xi(z)}$]$_z$ where each of $R_{i(q)}$ and $R_{xi(z)}$ is an amino acid side chain. Where q is between 1 and 10, the moiety can have between 1 and 10 amino acid residues (monomer to decamer). Each amino acid side chain is selected independently, and there may be two separate amino acid sequences, one represented by moiety $R_4$ and the other by moiety $R_6$. Therefore, the amino acid side chains between $R_i(1)$ and $R_i(q)$ are amino acid side chains $R_{i(1)}$ through $R_{i(10)}$ where q=10. For moiety $R_6$, the amino acid side chains are between $R_{xi(11)}$ and $R_{xi(21)}$, where z=10, to avoid duplicating amino acid side chains $R_{i(1)}$ through $R_{i(10)}$. For example, if q=3, then $R_4$ is —(NHCHR$_1$CO)—(NHCHR$_2$CO)—(NHCHR$_3$CO)—, and if z=4, $R_6$ is [(C=O)CHR$_{11}$—NH]—[(C=O)CHR$_{12}$—NH]—[(C=O)CHR$_{13}$—NH]—[(C=O)CHR$_{14}$—NH]—

The advantages of the invention include a highly flexible synthetic strategy which allows a wide variety of structures to be easily introduced into the target product, even when using combinatorial or matrix synthetic methods to provide diverse libraries for high throughput screening including but not limited to the inhibition of enzymes. Illustrative examples of the synthetic methods and compounds of the invention are provided in the section below. For example, a single DL amino acid ester was reacted with a mixture of three different aldehydes to yield a library of six components. The presence of various members of a library was established by HPLC or MS or both. In some cases the $^{13}$C NMR carbonyl absorptions and molecular ion peaks (MS) of the library were compared with those obtained from individually- or conventionally-synthesized members.

The disclosed synthesis features two strategic steps. First, a reductive amination of a carbonyl-containing compound with an amino acid allows introduction of a wide variety of structures for $R_3$ and $R_4$ based on the aldehyde, ketone, or other carbonyl-analog containing compound (Schemes 1 and 2). Second, a chloromethylation procedure using the bisulfite adduct of formaldehyde and thionyl chloride allows combinatorial synthesis in solution phase (Scheme 5), which improves the high volume production of libraries or large scale production of individual compounds. The disclosed chloromethylation procedure not only uses fewer synthetic steps and less expensive reagents, but also avoid costly chromatographic purification, thereby improving the high volume production of libraries and the large scale production of individual compounds. For example, yields using 5 equivalents of the bisulfite adduct were between 80% and 90% where $R_5$=H and $R_6$ is Cl in the imide H-1. In addition, the multi-component Ugi reaction generates a library with diverse members. For example, a carboxylic acid $R_1$—COOH introduces $R_1$, $R_2$ is introduced by the amino reagent, $R_3$ and $R_4$ by the ketone, and/or $R_5$ by the cyano reagent. The Ugi reaction is described, for example, in Demharter et al. (1996) *Angew. Chem. Int. Ed,* 35:173–175.

Terms

Some terms are defined below and elsewhere in the disclosure.

Alkyls may be substituted or unsubstituted and may be straight, branched, or cyclic. Preferably, alkyl groups are between 1 and 10 carbon atoms, and more preferably between 1 and 6 carbon atoms. Examples of alkyls include methyl, ethyl, propyl, isopropyl, butyl, isobutyl, sec-butyl, t-butyl, pentyl, cyclopentyl, isopentyl, neopentyl, t-pentyl, sec-pentyl, hexyl, cyclohexyl, isohexyl, 2,3-dimethylbutyl, 2,2-dimethylbutyl, 3-ethylpentyl, 3,4-dimethylpentyl, heptyl, octyl, nonyl, decyl, and (2,3,4-trimethylcyclohexyl) methyl. An alkylene is a bivalent hydrocarbon, e.g., an alkyl group with an additional hydrogen removed, such as methylene, propylene, or 1,4-cyclohexylene. Alkoxy groups are alkyl groups terminated by an oxygen. Alkoxy groups also include polyethers, such as methoxyethoxy.

Alkenyls are alkyl groups with one or more unsaturated carbon-carbon bonds, such as cyclopentenyl, cyclopentadienyl, cyclohexadiene, but-2-enyl, 3,4-dimethylpent-3-enyl, allyl, vinyl, prenyl, and isoprenyl. Alkenylenes include vinylene and propenylene.

Amino acid side chains include the side chains of natural and non-natural amino acids, which may be protected or unprotected, or otherwise modified. Natural amino acids include glycine, alanine, valine, leucine, isoleucine, serine, threonine, aspartic acid, asparagine, lysine, glutamic acid, glutamine, arginine, histidine, phenylalanine, cysteine, tryptophan, tyrosine, methionine, and proline. Others include lanthionine, cystathionine, and homoserine. Some unusual or modified amino acids include 2-aminoadipic acid, 3-aminoadipic acid, beta-alanine, 2-aminobutyric acid, 4-aminobutyric acid, 6-amino-caproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, 6-N-methyllysine, N-methylvaline, norvaline, norleucine, and ornithine. Non-natural amino acids include 1-aminosuberic acid, 3-benzothienylalanine, 4,4'-biphenylalanine, 4-bromophenylalanine, 2-chlorophenylalanine, 3-chlorophenylalanine, 4-chlorophenylalanine, 3-cyanophenylalanine, 4-cyanophenylalanine, 3,4-dichlorophenylalanine, 3,4-difluorophenylalanine, 3,5-difluorophenylalanine, 2-fluorophenylalanine, 3-fluorophenylalanine, 4-fluorophenylalanine, 3,3-diphenylalanine, homophenylalanine, 2-indanylglycine, 4-iodophenylalanine, 1-naphthylalanine, 2-naphthylalanine, 4-nitrophenylalanine, pentafluorophenylalanine, 2-pyridylalanine, 3-pyridylalanine, 4-pyridylalanine, tetrahydroisoquinoline-3—COOH, 4-thiazolalanine, 2-thienylalanine, 3-trifluoroethylphenylalanine, 4-trifluoromethylphenylalanine, and 3,4,5-trifluoromethylphenylalanine. The term "side chain" is well known in the art; for example, the side chains of leucine and phenylalanine are isobutyl (or 2-methylpropyl) and benzyl, respectively.

Protected amino acid side chains are side chains that have reactive functionalities such as hydroxyl (Ser, Thr), thiol (Cys), carboxylic acid (e.g., Asp, Glu, or any C-terminal amino acid), or amino (e.g., Asn, Gln, Lys, Arg, and any free N-terminal amino acid) which are masked by a protecting group. For example, a hydroxyl group can be protected as an ether or ester, a thiol group can be protected as a thioether or thioester, a carboxylic acid can be protected as an ester, amide, or hydrazide, and an amino group can be protected as a carbamate or amide. Methods of protecting and deprotecting (or deblocking) a functionality are well-known to those in the art and described in detail in, e.g., *Protective Groups in Organic Synthesis,* edited by T. W. Greene and P. G. M. Wuts, John Wiley & Sons (1991).

Amino protecting groups ("G") include carbamates and amides. Carbamates include methyl, ethyl, 9-fluorenylmethyl, 9-(2-sulfo)fluorenylmethyl, 9-(2,7-dibromo)fluorenylmethyl, 2,7-di-t-butyl[9-(10,10-dioxo-10,10,10,10-tetrahydrothioxanthyl)]methyl, and 4-methoxyphenacyl. Others include 2,2,2-trichloroethyl, 2-trimethysilylethyl, 2-phenylethyl, t-butyl, vinyl, allyl, cinnamyl, benzyl, and substituted benzyls, 2-methylthioethyl. Amides include N-formyl, N-acetyl, N-chloroacetyl, N-trichloroacetyl, N-trifluoroacetyl, N-phenylacetyl, N-3-pyridylcarboxamide, and N-benzoyl.

Carboxyl protecting groups ("J") include substituted methyl esters, 2-substituted ethyl esters, substituted benzyl esters, silyl esters, and activated esters. Examples include 9-fluorenylmethyl, methoxymethyl, methylthiomethyl, tetrahydropyranyl, tetrahydrofuranyl, methoxyethoxymethyl, 2-(trimethyl-silyl)ethoxymethyl, benzyloxymethyl, phenacyl, p-bromophenacyl, alpha-methylphenacyl, p-methoxyphenacyl, carboxamidomethyl, N-phthalimidomethyl, 2,2,2-trichloroethyl, 2-haloethyl, omega-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, methylcinnamyl, phenyl, p-(methylmercapto)phenyl, benzyl, triphenylmethyl, diphenylmethyl, bis(o-nitrophenyl)methyl, 9-anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, piperonyl, 4-picolyl, trimethylsilyl, triethylsilyl, t-butyldimethylsilyl, i-propyldimethylsilyl, phenyldimethylsilyl, di-t-butylmethylsilyl, and thiols.

Aryls include aromatic rings, substituted or unsubstituted, preferably having between 6 and 15 carbon atoms, and more preferably between 6 and 12 carbon atoms. Examples of aryls include as phenyl, naphthyl, and indene, pentalene, anthracene, azulene, and biphenylene. Alkylaryls include tolyl, xylyl, mesityl, cumenyl, 2-ethyl-4 methylphenyl. Arylalkyls include benzyl, phenylethyl, and arylenes include 1,4-phenylene.

An enzyme inhibitor can be a competitive inhibitor, a noncompetitive inhibitor, or a suicide inhibitor (the latter is also known as a mechanism-based inhibitor). Inhibition is measured by methods known to those in the art and is variously expressed as $K_I$ (micromolar), $k_{inact}/K_I M^{-1}s^{-1}$, or percent inhibition (relative to absence of inhibitor compound). Preferably, percent inhibition is at least 25%, e.g., at least 30%, or at least 40%. Suicide inhibitors or mechanism-based inhibitors have a reactive functionality that forms a covalent bond with the target. Some of the disclosed compounds are both synthetic intermediates and suicide inhibitors.

Heterocyclic radicals may be aromatic (heteroaryl) or nonaromatic, and substituted or unsubstituted. Preferably, they have between 1 and 2 rings, are single, fused or bridged rings, and contain between 2 and 15 carbon atoms in the ring, i.e., exclusive of substitution. Heterocycles include thienyl, furyl, pyranyl, isobenzofuranyl, 2H-pyrrolyl, pyrrolyl, imidazolyl, pyrazolyl, isothiazolyl, oxadiazolyl, oxazolyl, thiadiazolyl, thiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzainyl, furazanyl, pyrrolinyl, pyrrolidinyl, imidazolidinyl, imidazolinyl, piperidyl, piperazinyl, and morpholinyl.

Lactones are cyclic esters, preferably having between 4 and 8 ring atoms. Lactones can be substituted with hydroxyl, amino, halogen, alkyl, alkoxy, alkenyl, alkenyloxy, aryl, or heterocyclic radical. Substituted lactones include polycyclic moieties with a fused ring, such as phthalides which have a fused aromatic ring. For example, $R_5$ and $R_6$ taken together can be a substituted phthalide. Lactones are added by, e.g., using an electronegative nitrogen on the template ring to displace a halide, such as bromide, on the lactone reagent.

Oxa acids increase polarity, and in turn water-solubility and bioavailability. According to the invention, an oxa acid moiety can be added to a template wherever an amide linkage is formed (see FIG. 1b).

Polymer (Pn) includes biocompatible polymers or copolymers having a molecular weight between 100 and 50,000, and preferably between 500 and 5,000 (e.g., between 500 and 2,500, between 1000 and 4,000, or between 2000 and 5,000). Pn is a polymer, block copolymer, or copolymer including one or more of the following polymers: polylysine, polylactate, polyurethane, polycarbonate, polyurea, polypropylene, nylon, polyester, and polystyrene. Pn can be loaded with one or more of the disclosed compounds, for example, by a covalent linkage such as amido, urethane, urea, ether, or ester. Pn is loaded with between 0.5% and 25% or more of a disclosed composition (e.g., between 5% and 15%, or between 10% and 25%). Where the disclosed composition is itself an inhibitor-polymer, the Pn polymer and the inhibitor polymer need not be covalently bonded, and may be a mixture (chain entangled) held together by hydrophobic/hydrophilic interactions, H-bonds, and other non-covalent forces. Block copolymers may also be formed with alternating segments of one or more disclosed composition (A, B) and one or more Pn polymers (C, D). Examples include ABCABDA, AACCBBDDAA, and $(AB)_n(C)_m$. The polymer Pn can also be used as a matrix for synthesizing the compound (e.g., a bead, film, or rod support), or as a supporting matrix for analytical, diagnostic, or therapeutic methods, including controlled release formulations. Pharmaceutical formulations include embodiments where the polymer Pn is not covalently bonded to the disclosed inhibitors, which diffuse out of the polymer matrix in a manner dependent upon time, temperature, solvent, solute, pH, or enzymatic activity.

Substituting moieties have one, two, three, or more of the following moieties (instead of a hydrogen): alkyl, alkenyl, alkoxy, alkenyloxy, haloalkyl, haloalkoxy, hydroxy, nitro, chloro, fluoro, bromo, and iodo. In some embodiments, substituting moieties include thiol, cyano, and amino. Preferably, substituting moieties have between 1 and 6 carbon atoms, and more preferably between 1 and 3 carbon atoms, if any. Examples of carbon-containing substitutions include chloromethyl, hydroxymethyl, bromoethyl, methoxy, and ethoxy. An alkyl does not have an alkyl or haloalkyl substituent, although a cycloalkyl may have an alkyl or haloalkyl substituent.

The synthesis of representative inhibitors is described next.

II. Synthesis

Individual compounds or libraries based on E-1 were obtained as illustrated in Scheme 1, using the following general procedures Groutas et al. (1997) *Biochemistry* 36, 4739–4750.

EXAMPLE 1

Compounds B-1 and C-1

An amino acid ester hydrochloride A-1 (1 eq) in dry methylene chloride was treated with triethylamine (3 eq), followed by the portionwise addition of sulfamoyl chloride (2 eq). Stirring for 3 h at room temperature and work up yielded B-1. Examples of precursor amino acid esters used in generating B-1 include those derived from Ala, Val, Leu, Phe, Met, Asp and Lys. The reaction was also carried out using amino acid esters. The resulting mixtures were elaborated further to yield libraries.

A B-1 derivative (1 eq) in dry THF was treated with 60% sodium hydride (2 eq) at room temperature under a nitrogen atmosphere. After stirring for 3 h, the solvent was evaporated and the residue triturated with hexane yielding the disodium salt. Acidification to pH~1 using concentrated HCl, followed by work up, yielded C-1. The reaction was also carried out using mixtures of B-1 to yield libraries.

C-1 was elaborated further (Scheme 1) to yield D-1 and E-1 either as single compounds or libraries, as illustrated below. The proton and carbon NMR spectra were recorded on a Varian XL300 NMR spectrometer.

EXAMPLE 2

Compound D-1a

Triethylamine (2.22 g; 22 mmol) was added to a solution of (S)-4-isobutyl 1,2,5-thiadiazolidin-3-one 1,1 dioxide (3.84 g; 20 mmol) in dry acetonitrile (35 mL), followed by t-butyl bromoacetate (4.26 g; 22 mmol). The reaction mixture was refluxed overnight with stirring. The solvent was removed in vacuo and the residue taken up in ethyl acetate (30 mL) and washed with water (30 mL), 5% HCl (2×25 mL) and brine (30 mL), and dried over anhydrous sodium sulfate. The solvent was then removed and the crude product was purified using flash chromatography (silica gel/diethyl ether). Compound D-1a was obtained in 46% yield (2.05 g). $^1$H NMR (CDCl$_3$): δ0.98 (dd,6H), 1.48 (s,9H), 1.70–1.92 (m,3H), 4.18 (s,2H), 4.26 (dd,1H). $^{13}$C NMR: δ21.1, 22.8, 25.0, 27.8, 39.9, 41.6, 59.7, 83.6, 165.0, 169.5. Groutas, W. C. et al. (1994) *Biochem. Biophys. Res. Comm.* 198, 341–349; Groutas et al. (1997) *Biochemistry* 36, 4739–4750; Auf, N. et al. (1991) *Tetrahedron Lett.* 32, 6545–6546; Dewynter, G. et al. (1993) *Tetrahedron* 49, 65–76; Dewynter, G. (1996) ibid. 52, 993–1004.

EXAMPLE 3

Compound D-1b

Compound D-1b was prepared from (S)-4-Benzyl-1,2,5-thiadiazolidin-3-one 1,1 dioxide in 71 % yield using a procedure similar to the one used in the preparation of D-1a. $^1$H NMR (DMSO-d$_6$): δ1.45 (s,9H), 2.90 (dd,1H), 3.21 (dd,1H), 4.23 (s,2H), 4.57 (dd,1H), 7.23–7.37 (m,5H), 8.75 (br s, 1H). $^{13}$C NMR: δ27.47, 38.69, 41.15, 61.10, 82.04, 126.63, 128.19, 129.22,136.42, 164.73, 168.41.

EXAMPLE 4

Compound E-1a

A solution of compound D-1a (1.86 g; 6.05 mmol) in dry acetonitrile (40 mL) was treated with NaH (0.29 g; 7.26 mmol), followed by t-butyl bromoacetate (1.30 g; 6.7 mmol). The reaction mixture was stirred overnight at room temperature. The solvent was removed and the residue was taken up in ethyl acetate (80 mL), washed with water (3×50 mL) and dried over anhydrous sodiumسسسسسسسسس sulfate. Evaporation of the solvent left a pure product E-1a (2.56 g; 100% yield). $^1$H NMR (CDCl$_3$): δ1.00 (t,6H), 1.48 (s,9H), 1.49 (s,9H), 1.75–1.95 (m,3H), 3.78 (d,1H), 4.11 (d,1H), 4.12 (d,1H), 4.27 (d,1H), 4.28(d,1H). $^{13}$C NMR: δ21.79, 22.82, 24.70, 27.92, 40.93, 41.65, 49.40, 64.54, 83.21, 83.43,164.22, 166.78, 167.45.

EXAMPLE 5

Compound E-1b

Compound E-1b was obtained in 87% yield starting with compound D-1b using a procedure similar to that used in the preparation of E-1a. $^1$H NMR (CDCl$_3$): δ1.40 (s,9H), 1.50 (s,9H), 2.99 (d,1H), 3.82 (d,1H), 3.09 (dd,1H), 3.33 (dd,1H), 4.21 (dd,2H), 4.40 (d,1H), 7.32 (m,5H). $^{13}$C NMR: δ27.85, 27.93, 38.61, 41.79, 49.49, 67.62, 83.27, 83.32, 127.39, 128.89, 129.31, 135.94, 164.14, 166.36, 166.75.

EXAMPLE 6

Compound E-1c

Compound E-1a (2.56 g; 6 mmol) in dry methylene chloride (6 mL) was treated with trifluoroacetic acid (TFA) (6 m/L) and stirred for 4 h at room temperature under nitrogen. The solvent and excess TFA were removed in vacuo, leaving a pure product E-1c (1.91 g; 100% yield). $^1$H NMR (DMSO-d$_6$): δ0.94 (dd,6H), 1.60–1.90 (m,3H), 4.10 (d,2H), 4.25 (d,2H), 4.37 (t,1H). $^{13}$C NMR: δ22.21, 22.47, 24.02, 40.28, 40.72, 48.92, 64.34, 166.85, 167.63, 169.58.

EXAMPLE 7

Compound E-1d

Diacid E-1d was obtained from E-1b using a procedure similar to that used in the preparation of E-1c. NMR (DMSO-d$_6$): δ3.10 (ddd,2H), 3.60 (d,1H), 3.98 (d,1H), 4.22 (d,2H), 4.77 (dd,1H), 7.28 (m,5H). $^{13}$C NMR: δ37.37, 40.85, 48.43, 66.22, 126.92, 128.31, 129.68, 135.74, 166.60, 166.99, 169.50.

EXAMPLE 8

Compounds E-1e and E-1f

Diacid E-1c (3.11 g; 10 mmol) was mixed with thionyl chloride (20 mL) and five drops of dimethyl formamide, and refluxed for 1 h with stirring. Excess thionyl chloride was then removed in vacuo, yielding 3.47 g (100% yield) of the diacid chloride E-1e. $^1$H NMR (CDCl$_3$): δ1.00 (t, 6H), 1.75–1.95 (m, 3H), 4.19 (t, 1H), 4.30 (d, 1H), 4.68 (d,1H), 4.69 (dd,2H). $^{13}$C NMR: δ21.80, 22.68, 24.69, 40.79, 49.12, 57.85, 64.82, 166.26, 166.56, 169.95.

Diacid chloride E-1f was obtained from E-1d using a similar procedure.

EXAMPLE 9

Compound E-1g

A solution of diacid chloride E-1e (0.35 g; 1 mmol) in methylene chloride (15 mL) was treated with phenethylamine (0.27 g; 2.20 mmol) and triethylamine (0.22 g; 2.20 mmol), and the mixture stirred for 1 h. An additional amount of CH$_2$Cl$_2$ (20 mL) was added and the reaction mixture was extracted with 5% HCl (10 mL) and 5% NaHCO$_3$ (10 mL). Removal of the solvent left a crude product which was purified by flash chromatography, yielding 0.24 g (47% yield) of compound E-1g. $^1$H NMR (CDCl$_3$/CD$_3$COCD$_3$): δ0.98 (t,6H), 1.62–1.96 (m,3H), 2.82 (m,4H), 3.97 (m,4H), 3.90 (d,1H), 4.40 (d,1H), 4.02 (d,1H), 4.31 (d,1H), 4.18 (dd,1H), 7.11–7.30 (m,10H), 7.53 (br t,1H), 7.90 (br t,1H).

$^{13}$C NMR: δ22.29, 22.91, 24.28, 28.77, 34.83, 35.06, 40.39, 40.56, 40.79, 41.98, 51.70, 65.12, 125.61, 125.96, 127.82, 127.94, 128.01, 128.12, 138.00, 138.58, 164.84, 165.57, 167.77.

EXAMPLE 10
Compounds E-1h and E-1i

To a mixture of compound E-1e (0.35 g; 1 mmol) and L-Phe-OCH$_3$ hydrochloride (0.48 g; 2.22 mmol) in methylene chloride (15 mL) was added triethylamine (0.45 g; 4.46 mmol). After stirring the solution for 2 h at room temperature, the solvent was removed and the residue dissolved in ether (40 mL). Following work up and purification, there was obtained compound E-1h in 67% yield (0.42 g). $^1$H NMR (CDCl$_3$): δ0.93 (t,6H), 1.76–1.90 (m,3H), 3.00 (dd,1H), 3.05 (d,2H), 3.18 (dd,1H), 3.68 (s,3H), 3.72 (s,3H), 3.89 (d,1H), 4.10 (t,1H), 4.16 (dd,2H), 4.82 (m,2H), 6.69 (br d,1H), 7.02–7.30 (m,10H), 7.42 (br d, 1H). $^{13}$C NMR: δ21.62, 22.76, 24.74, 37.51, 37.68, 40.72, 42.59, 51.34, 52.26, 52.50, 53.30, 54.05, 65.29, 126.93, 127.36, 128.46, 128.61, 128.74, 129.09, 129.18, 129.28, 135.11, 136.15, 165.03, 167.13, 167.50, 171.30.

Compound E-1i was obtained from E-1f and 2-phenethylamine using a similar procedure. $^1$H NMR (CDCl$_3$): δ2.71 (m,2H), 2.81 (t,2H), 2.95 (dd,1H), 3.27 (dd,1H), 2.96 (d,1H), 4.02 (d,1H), 3.35–3.60 (m,4H), 4.03 (d,1H), 4.33 (d,1H), 4.18 (dd,1H), 5.80 (br t, 1H), 7.03–7.35 (m,15H), 7.58 (br t, 1H). $^{13}$C NMR: δ35.20, 35.45, 37.82, 40.78, 41.34, 42.55, 68.96, 126.28, 126.77, 127.41, 128.41, 128.57, 128.69, 128.85, 129.28, 135.94, 137.90, 138.81, 165.24, 166.57, 167.65.

EXAMPLE 11
Libraries of E-1

A four-component library, E-1j, was constructed by adding dropwise a mixture of 2-phenethylamine (0.27 g; 2.2 mmol) and n-butylamine (0.16 g; 2.2 mmol) in 4 mL dry methylene chloride to a solution of compound E-1e (0.69 g; 2 mmol) and triethylamine (0.45 g; 4.4 mmol) in 10 mL methylene chloride. After stirring for 2 h at room temperature, the solvent was removed in vacuo and the residue partitioned with ethyl acetate (25 mL) and 10% HCl (10 mL). The organic layer was washed with 5% HCl (3×10 mL), 5% NaHCO$_3$ (3×10 mL) and brine (15 mL), and was then dried over anhydrous sodium sulfate. Removal of the solvent yielded library E-1j.

In an alternative synthesis, individual compounds or libraries of E-1 were generated according to Scheme 2 through compounds F-1, G-1 and H-1.

An amino acid ester hydrochloride (25 mmol) in dry 1,2-dichloroethane (50 mL) was treated with a carbonyl-containing compound (e.g., aldehyde, ketone, α-ketoester), or a carbonyl analog-containing compound such as oxoalkyl phosphonate) (26 mmol) in 1,2-dichloroethane (15 mL). After stirring for 1 h at room temperature, glacial acetic acid (3 g) was added, followed by sodium triacetoxyborohydride (50 mmol). The reaction mixture was stirred overnight at room temperature. Work up yielded reductive amination product F-1. Abdel-Magid, A. F. et al. (1996) *J. Org. Chem.* 61, 3849–3862; Szardenings, A. K. et al. (1996) ibid. 61, 6720–6722; Ramanjulu, J. M. & Joullie, M. M. (1996) *Synth. Comm.* 26, 1379–1384; Ryglowski, A. & Kafarski, P. (1996) *Tetrahedron* 52, 10685–10692.

The reductive amination procedure was also carried out using mixtures of amino acid esters with mixtures of aldehydes. The products were subsequently used to construct libraries.

Elaboration of F-1 to generate G-1 and H-1 (Scheme 2) was carried out as described for B-1 and C-1 (Scheme 1). G-1 and H-1 were subsequently transformed into derivatives of E-1.

EXAMPLE 12
Compound F-1a (L)-Leu-OCH$_3$ hydrochloride (1.36 g; 7.5 mmol) in 30 mL 1,2-dichloroethane was mixed with BocNHCH$_2$CHO (1.27 g; 8 mmol) under nitrogen. After stirring the mixture for 0.5 h, glacial acetic acid (0.6 g) and sodium (triacetoxy) borohydride (2.23 g; 10.5 mmol) were added. The reaction mixture was stirred for 16 h at room temperature and worked up by adding saturated NaHCO$_3$ (80 mL). After the organic phase was separated, the aqueous solution was extracted with ether (3×75 mL) and the organic extracts were combined. The combined organic extract was washed with saturated NaHCO$_3$ and brine, and dried over anhydrous sodium sulfate. Removal of the solvent left a quantitative yield of an oily product F-1a. $^1$H NMR (CDCl$_3$): δ0.91 (dd,6H), 1.44 (s,9H), 1.6–1.8 (m,3H), 2.53 (m,1H), 2.76 (m,1H), 3.1–3.3 (m,4H), 3.72 (s,3H). $^{13}$C NMR: δ155.99 and 176.24 (C═O). The product was used in the next step.

EXAMPLE 13
Compound G-1a

Secondary amine F-1a (2.16 g; 7.5 mmol) obtained above was dissolved in dry methylene chloride (15 mL) and then treated with triethylamine (1.52 g; 15 mmol). The solution was cooled to 0° C. and sulfamoyl chloride (1.73 g; 15 mmol) was added and the reaction stirred at RT for 16 h. The solvent was removed and ether or ethyl acetate (30 mL) and 5% HCl (30 mL) added. The organic phase was separated and washed with 5% HCl (20 mL) and brine (25 mL), and dried over anhydrous sodium sulfate. Evaporation of the solvent left a product G-1a(1.43 g; 52% yield) ($^{13}$C NMR (CDCl$_3$): δ173.13 & 156.14 (C═O) which was used in the next step without further purification.

EXAMPLE 14
Compound H-1a

The sulfamide ester (1.37 g; 3.73 mmol) was dissolved in dry THF (8 mL) and then treated with 60% sodium hydride (0.16 g; 4.47 mmol) at RT under a nitrogen atmosphere. After the solution was stirred overnight, the solvent was removed in vacuo and the residue triturated with hexane. The precipitated salt was filtered and washed with ether, yielding product H-1a (1.23 g; 93% yield) ($^{13}$C NMR (CDCl$_3$): δ179.16, 156.72 (C═O)).

EXAMPLE 15
Compound E-1k

Sodium salt H-1a (1.13 g; 3.15 mmol) was suspended in 5 mL dry toluene and tetra-n-butyl ammonium bromide (0.10 g; 0.3 mmol) and benzyl bromoacetate (0.79 g; 3.45 mmol) were added and the solution was refluxed for 24 h. The solvent was removed and methylene chloride added to the residue. The solution was filtered through silica gel, the filtrate was evaporated and the crude product E-1k purified by flash chromatography using silica gel and a hexane/ether gradient (0.39 g; 26% yield). $^1$H NMR (CDCl$_3$): δ0.95 (dd,6H), 1.45 (s,9H), 1.78 (m,2H), 1.92 (m,1H), 3.28–3.55 (m,4H), 4.08 (t,1H), 4.32 (s,2H), 5.07 (br t, 1H), 5.21 (s,2H), 7.34 (m,5H). $^{13}$C NMR: δ22.36, 24.34, 28.26, 39.03, 39.64, 40.42, 47.87, 64.77, 67.89, 79.71, 128.28, 128.37, 128.57, 134.59, 155.78, 165.38, 166.84. This derivative of E-1, E-1k, can be readily deblocked and elaborated further to yield additional inhibitors.

Other variants of E-1 were generated from I-1 (Scheme 3) using the Mitsunobu reaction, followed by alkylation. Likewise, C-1 & H-1 were used to generate derivatives of E-1 using the Mitsunobu reaction (Scheme 4).

EXAMPLE 16
Compounds E-1l and E-1m (L)-4-Benzyl-1,2,5-thiadiazolidin-3-one 1,1 dioxide (1.13 g; 5 mmol), triphenyl phosphine (1.5 g; 5.72 mmol) and Boc-L-serine methyl ester (1.21 g; 5.52 mmol) were dissolved in 10 mL dry THF and the solution cooled in an ice bath. Diethylazodicarboxylate (DEAD) (1.0 g; 5.74 mmol) in 3 mL THF was added dropwise and the reaction mixture allowed to reach RT. After stirring for 20 h the solvent was removed in vacuo and the residue taken up in ethyl acetate (50 mL) and washed in succession with saturated $NaHCO_3$, 5% $NaHCO_3$, 5% HCl and brine. The organic layer was dried and then evaporated. The residue was dissolved in ether (40 mL). On cooling the solution to 0° C., the triphenyl-phosphine oxide precipitate was filtered off. The solution was evaporated in vacuo and the residue flash chromatographed using silica gel and a gradient of hexane/ethyl acetate, yielding compound E-1l (0.47 g; 22% yield) and compound E-1m (0.19 g; 6% yield). E-1l ($^1$H NMR/$CDCl_3$): δ1.47 (s,9H), 3.00 (dd,1H), 3.18 (dd,1H), 3.80 (s,3H), 4.58 (m,1H), 4.70 (br s,3H), 5.13 (d1H), 5.29 (d,1H), 7.19–7.30 (m,5H). $^{13}$C NMR: δ28.25, 37.99, 55.58, 53.12, 62.69, 71.94, 80.82, 127.65, 128.97, 129.14, 134.92, 155.00, 169.27, 176.83. E-1m ($^1$H NMR: δ1.43 (s,18H), 3.04 (dd, 1H), 3.27 (dd,1H), 3.75 (s,6H), 3.80–4.05 (m,5H), 5.39 (br m, 2H), 4.58 (m,1H), 5.58 (m,1H), 7.22–7.48 (m,5H). $^{13}$C NMR: δ28.18, 36.89, 42.38, 52.30, 52.45, 52.80, 55.66, 61.78, 63.14, 80.24, 80.40, 127.37, 128.75, 129.30, 135.21, 155.13, 155.70, 168.92, 169.92, 171.36.

Additional derivatives of E-1 can be obtained by removing the Boc group using trifluoroacetic acid and reacting the resulting amine with various functionalities, including acid chlorides, sulfonyl chlorides and isocyanates.

EXAMPLE 17
Compound D-1c

Diethylazodicarboxylate (5.22 g; 30 mmol) was added dropwise to a mixture of (L)-4-Benzyl 1,2,4-thiadiazolidin-3-one 1,1 dioxide (3.84 g; 20 mmol), Boc-glycinol (3.2 g; 20 mmol) and triphenyl phosphine (10.5 g; 40 mmol) at 0° C. with stirring. The reaction mixture was allowed to stir at room temperature for 15 h. The solvent was removed and the crude product was purified by flash chromatography, yielding 2.93 g (44%) of (L)-4-Benzyl-2-{(2-t-butoxycarbonyl) ethylamino}-1,2,4-thiadiazolidin-3-one 1,1dioxide, D-1c. $^1$H NMR($CDCl_3$): δ0.97 (dd,6H), 1.43 (s,9H), 1.63–1.95 (m,3H), 3.42 (m,2H), 3.72 (br m, 2H), 4.21 (br d, 1H), 5.05 (br s, 1H), 5.27 (br s,1H). $^{13}$C NMR: δ21.01, 22.84, 24.98, 28.29, 38.64, 39.92, 41.13, 59.37, 79.81, 155.98, 156.15, 169.79.

EXAMPLE 18
Compound E-1n

A solution of compound D-1c (2.8 g; 8.35 mmol) and benzyl 2-bromoacetate (2.29 g; 10 mmol) in 10 mL dry acetonitrile was treated with 60% sodium hydride (0.367 g; 9.85 mmol) at room temperature. The reaction mixture was stirred for 4 h at room temperature. After the solvent was removed, the residue was taken up in ethyl acetate (50 mL), washed with brine and dried. Removal of the solvent gave a crude product that was purified by flash chromatography using silica gel (ether/hexane 4:6), yielding 3.41 g (91%) pure product, E-1n.

Additional derivatives of E-1 can be obtained by removing, for example, the Boc group using trifluoroacetic acid and reacting the resulting amine with a range of functionalities, including acid chlorides, sulfonyl chlorides and isocyanates. Alternatively, removal of the benzyl group ($H_2$/Pd—C) yields the corresponding acid that can be elaborated further using standard synthetic methodology.

EXAMPLE 19
Compounds E-1o and E-1p

A derivative of H-1, (L)-4-isobutyl-5-benzyl-1,2,4-thiadiazolidin-3-one 1,1 dioxide (3.3 g; 11.7 mmol), t-butyl bromoacetate (2.52 g; 12.9 mmol) and triethylamine (1.30 g; 12.9 mmol) in 10 mL dry acetonitrile were stirred at room temperature overnight. The solvent was removed in vacuo and the residue was taken up in methylene chloride (30 mL) and washed with 5% HCl, water, 5% sodium bicarbonate and brine, and dried over anhydrous sodium sulfate. Evaporation of the solvent left a crude product which was purified by chromatography, yielding an oily product, E-1o (2.78 g; 60% yield). $^1$H NMR ($CDCl_3$): δ0.65 (d,3H), 0.79 (d,3H), 1.49 (s,9H), 1.56–1.82 (m,3H), 3.92 (t, 4.19 (s,2H), 4.29 (d,1H), 4.58 (d,1H), 7.38 (m,5H). $^{13}$C NMR: δ21.92, 22.33, 24.35, 27.91, 39.95, 41.39, 52.44, 63.24, 83.28, 128.74, 128.93, 129.15, 133.61, 164.37, 167.51.

Compound E-1o (1.1. g; 2.77 mmol) was stirred with trifluoroacetic acid (4 mL) in methylene chloride (2 mL) at room temperature for 10 h. Evaporation of the solvent and excess TFA yielded a pure product E-1p (0.94 g; 100%).

EXAMPLE 20
Compound E-1q

A solution of compound E-1p (0.8 g; 2.35 mmol), thionyl chloride (2.8 g; 23.5 mmol), methylene chloride (6 mL) and 2 drops of DMF was refluxed for 2 h. The solvent and unreacted reagent were removed in vacuo. The residue was dissolved in methylene chloride (10 mL) and treated with 2-phenethylamine (1.1 g; 9.08 mmol). After stirring the solution at room temperature for 48 h, it was washed with water, 5% HCl, 5% $NaHCO_3$ and brine. After drying over anhydrous sodium sulfate, the solvent was evaporated in vacuo and the crude residue was purified by chromatography, yielding E-1q (0.32 g; 34%). $^1$H NMR ($CDCl_3$): δ0.68 (d,3H), 0.78 (d,3H), 1.53–1.78 (m,3H), 2.82 (t,2H), 3.56 (q,2H), 3.91 4.18 (d,2H), 4.25 (d,1H), 4.51 (d,1H), 6.08 (br t, 1H), 7.18–7.32 (m,5H), 7.38 (s,5H). $^{13}$C NMR: δ22.05, 22.25, 24.35, 35.29, 39.73, 40.87, 42.99, 52.19, 63.19, 126.55, 128.63, 128.79, 128.93, 129.01, 129.21, 133.24, 138.39, 164.70, 167.50.

Individual derivatives (or mixtures) of H-1 were readily chloromethylated using formaldehyde sodium bisulfite addition compound and thionyl chloride, yielding E-1 compounds which are derivatives of J-1. The reaction worked equally efficiently using either the neutral compound(s) or the corresponding sodium salt(s). Further reaction with a nucleophilic species, including heterocyclic thiols, carboxylic acids and sulfonamides in the presence of base, yielded a range of mechanism-based inhibitors (Scheme 5). General procedures used are given below. The yields of the generated libraries ranged between 70–95% and the purity of the libraries was >90%.

EXAMPLE 21
Compound J-1 through chloromethylation

To a library of H-1 (5 mmol) was added thionyl chloride (10 mL), followed by formaldehyde sodium bisulfite addition compound (25 mmol) and the resulting mixture was heated at 70–75° C. for 20 h. Work up yielded libraries of J-1. Examples of libraries generated with their corresponding $^{13}$C NMR spectra (carbonyl group only) are listed in Table 1 (1–6). Abbreviations in Table 1 include trimethylacetaldehyde (TBU), p-methoxybenzaldehyde (PAA), and m-phenoxybenzaldehyde (MPA). A similar procedure was used to generate individual compounds.

EXAMPLE 22

Carboxylate and Sulfonamide Libraries of E-1

A library of J-1 (1 mmol) was dissolved in dry acetone, sodium iodide was added (2 mmol), and the resulting mixture was stirred overnight at room temperature. The solvent was then removed in vacuo, methylene chloride (2 mL) was added and the mixture filtered through silica gel. The silica gel was washed with methylene chloride (3 mL) and the combined filtrate was immediately treated with a solution of a carboxylic acid (2 mmol) and 1,8-Diazabicyclo [5.4.0]undecen-7-ene (DBU) (1.8 mmol) in methylene chloride (2 mL). The solution was stirred overnight at room temperature. Work up yielded a carboxylate library. The corresponding sulfonamide libraries were generated using an identical procedure. Examples of carboxylate (7–12) and sulfonamide (13–18) libraries generated are listed in Table 1. Examples of individual sulfonamides and oxaacid derivatives are listed in Tables 2 and 3, respectively.

TABLE 1

Inhibitors Derived from (DL)Ala, (DL)Leu, (DL)Phe where $R^5$ = H

| $R_6$ | | Cl (1–6) | | $OCOCH_3$ (7–12) | | $N(CO_2CH_3)SO_2CH_3$ (13–18) | | $SCH_2Phe(4-Cl)$ (19–24) | | $SO_2CH_2Phe(4-Cl)$ (25–30) |
|---|---|---|---|---|---|---|---|---|---|---|
| Ala | (1) | 165.726 | (7) | 166.203 | (13) | 165.060 | (19) | 166.438 | (25) | 166.528 |
| (TBU, PAA, MPA) | | 165.890 | | 166.307 | | 166.044 | | 166.622 | | 166.689 |
| | | 166.706 | | 167.136 | | 166.792 | | 166.297 | | 167.464 |
| Leu | (2) | 166.468 | (8) | 166.967 | (14) | 166.510 | (20) | 167.142 | (26) | 167.287 |
| (TBU, PAA, MPA) | | 166.601 | | 167.065 | | 166.643 | | 167.223 | | 167.302 |
| | | 166.666 | | 167.151 | | 166.723 | | 167.326 | | 167.409 |
| Phe | (3) | 166.186 | (9) | 166.636 | (15) | 164.907 | (21) | 165.777 | (27) | 165.889 |
| (TBU, PAA, MPA) | | 165.453 | | 165.701 | | 165.148 | | 166.017 | | 166.174 |
| | | 166.201 | | 166.575 | | 165.970 | | 166.602 | | 166.765 |
| TBU | (4) | 166.213 | (10) | 166.563 | (16) | 165.943 | (22) | 166.585 | (28) | 166.794 |
| (Ala, Leu, Phe) | | 166.616 | | 167.053 | | 166.507 | | 167.165 | | 167.358 |
| | | 166.692 | | 167.142 | | 166.792 | | 167.276 | | 167.492 |
| PAA | (5) | 165.456 | (11) | 165.910 | (17) | 165.127 | (23) | 166.064 | (29) | 166.142 |
| (Ala, Leu, Phe) | | 165.895 | | 166.409 | | 165.035 | | 166.679 | | 166.721 |
| | | 166.655 | | 167.157 | | 166.679 | | 167.375 | | 167.463 |
| MPA | (6) | 165.180 | (12) | 166.6401 | (18) | 164.904 | (24) | 165.677 | (30) | 165.895 |
| (Ala, Leu, Phe) | | 165.713 | | 166.225 | | 165.866 | | 166.400 | | 166.545 |
| | | 166.471 | | 166.970 | | 166.406 | | 167.053 | | 167.263 |

TABLE 2

Sulfonamide Derivatives of E-1

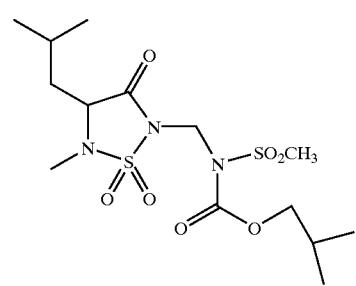

31

TABLE 2-continued

Sulfonamide Derivatives of E-1

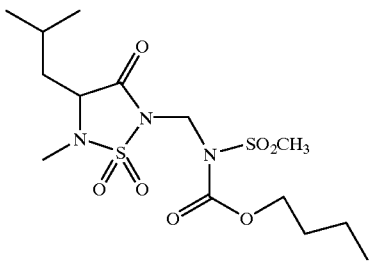

32

TABLE 2-continued

Sulfonamide Derivatives of E-1

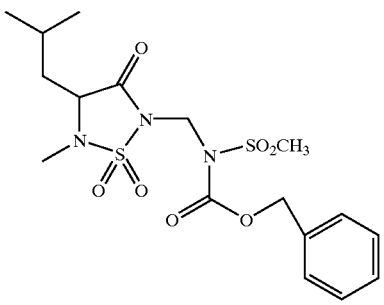

33

TABLE 2-continued
Sulfonamide Derivatives of E-1
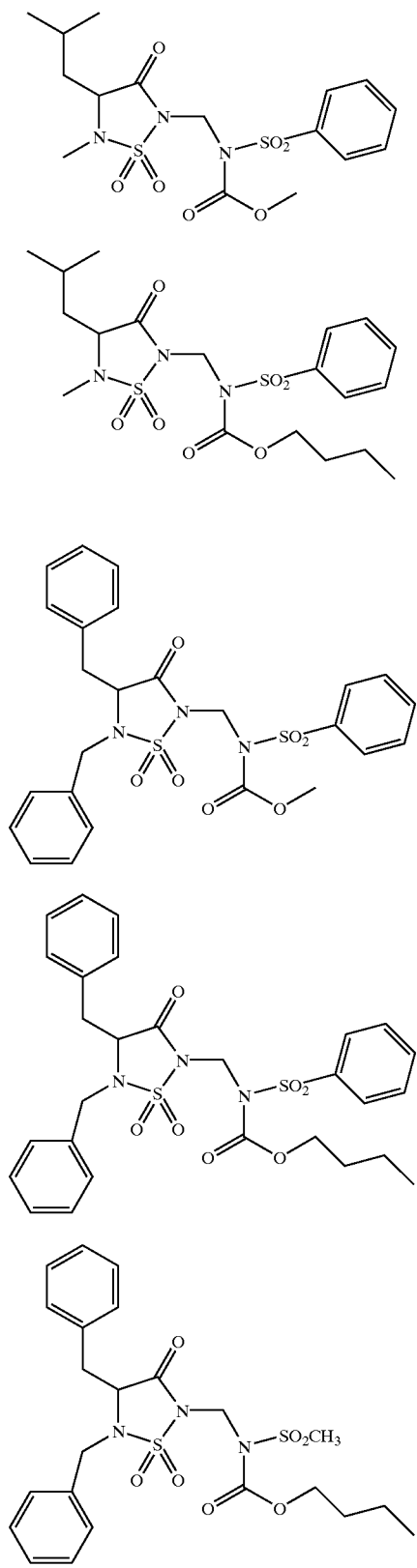
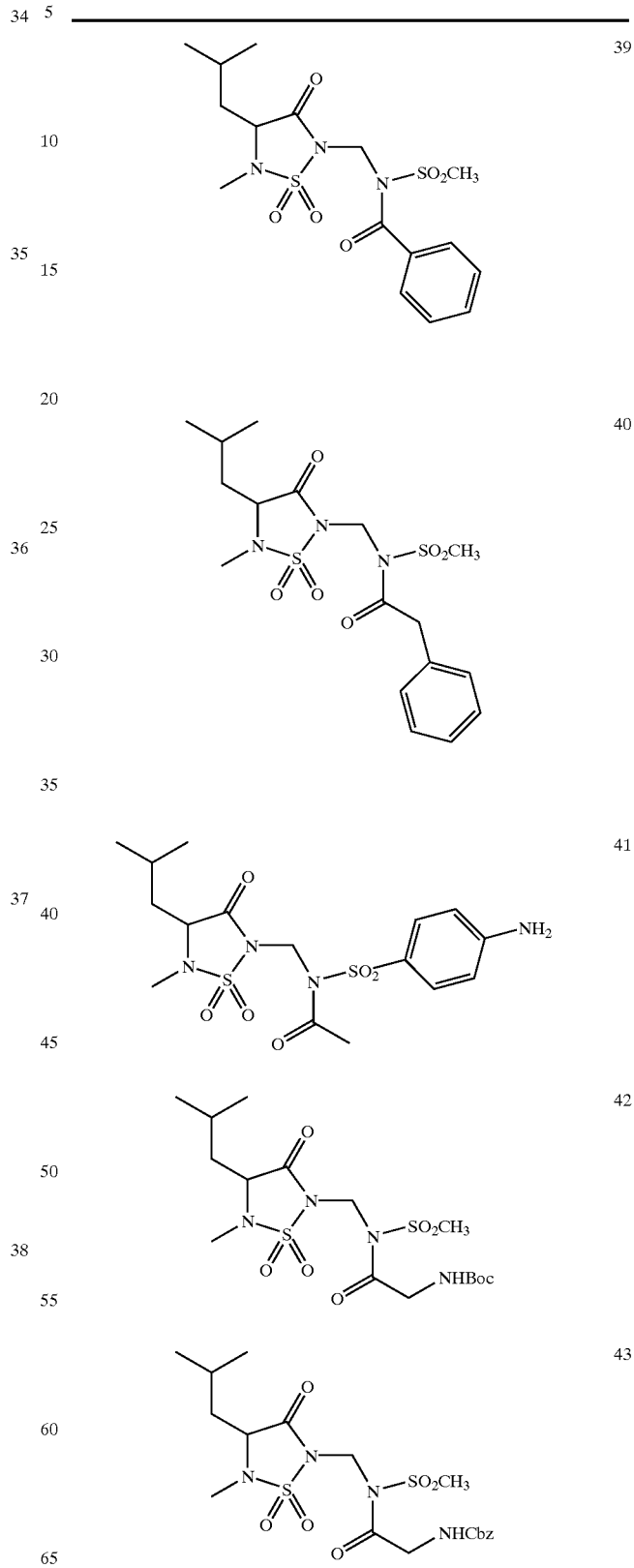

TABLE 2-continued
Sulfonamide Derivatives of E-1
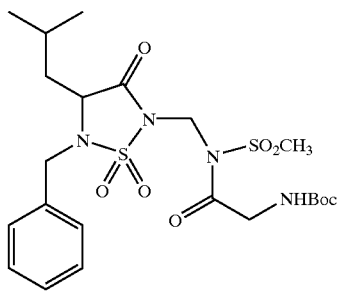
44
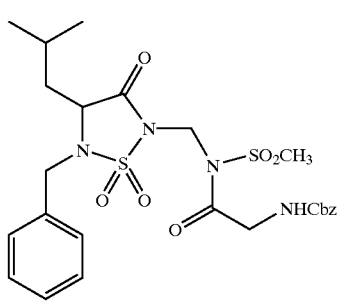
45
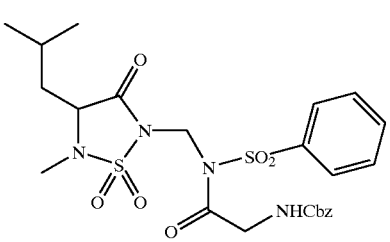
46
TABLE 2-continued
Sulfonamide Derivatives of E-1
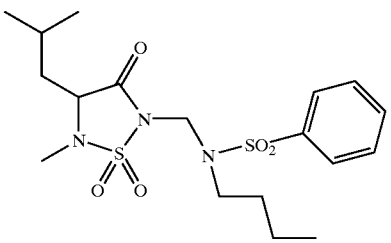
47
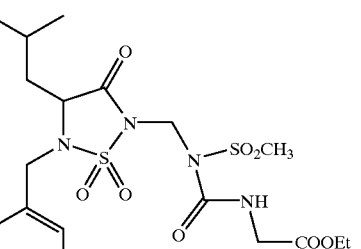
48
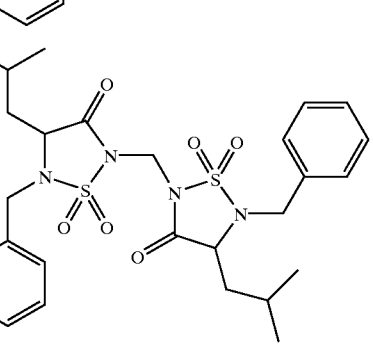
49
TABLE 3
Oxaacid Derivatives of E-1
| | $k_{inact}/K_I$ M$^{-1}$ s$^{-1}$ |
|---|---|
| 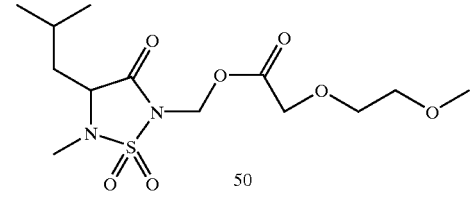 50 | 71,100 |
| 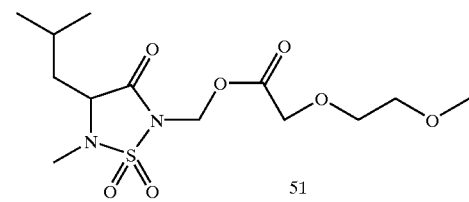 51 | 79,700 |

TABLE 3-continued

Oxaacid Derivatives of E-1

$k_{inact}/K_I$ M$^{-1}$ s$^{-1}$ 370,850

[Structure 52]

EXAMPLE 23

Sulfide Libraries of E-1

Triethylamine (2.2 mmol) was added to chloromethyl library J-1 (2 mmol) and a thiol (2.2 mmol) in dry acetonitrile (6 mL). The solution was stirred overnight at room temperature. Work up yielded the corresponding library (Table 1, 19–24). Examples of individual heterocyclic sulfides are listed in Table 4.

TABLE 4

Heterocyclic Sulfide Derivatives of E-1

[Structure 53]

[Structure 54]

[Structure 55]

TABLE 4-continued

Heterocyclic Sulfide Derivatives of E-1

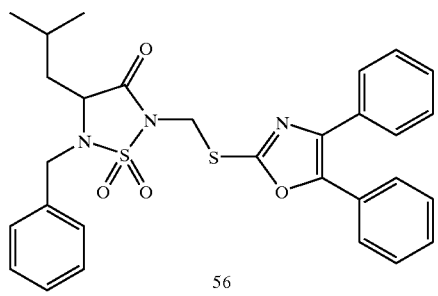

56

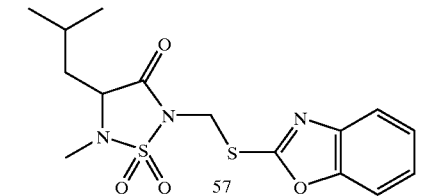

57

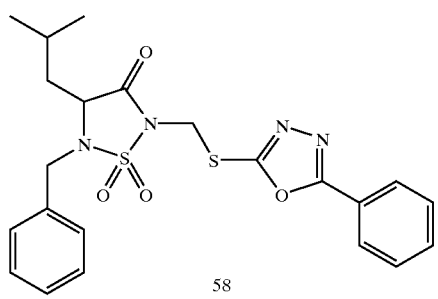

58

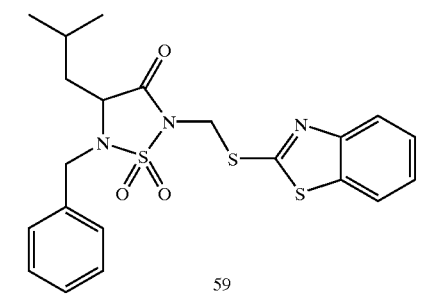

59

TABLE 4-continued
Heterocyclic Sulfide Derivatives of E-1
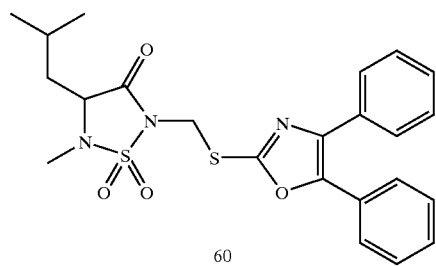
60
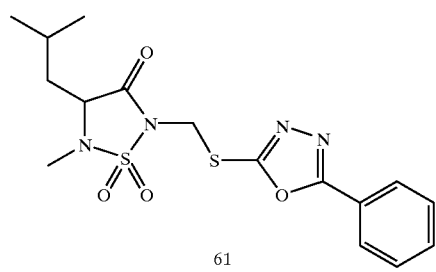
61
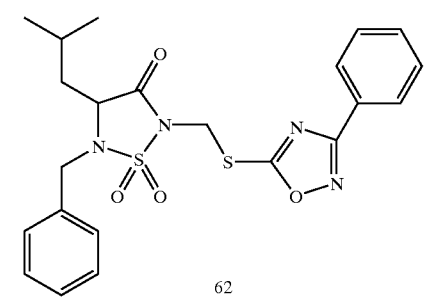
62
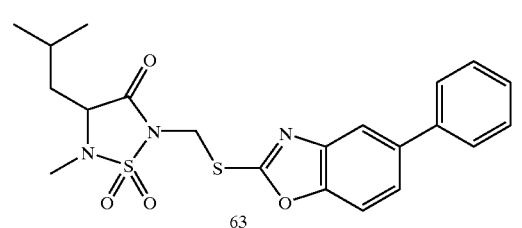
63
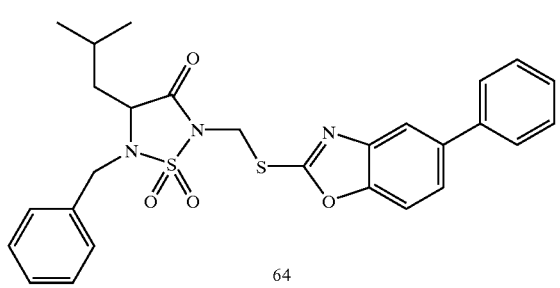
64
TABLE 4-continued
Heterocyclic Sulfide Derivatives of E-1
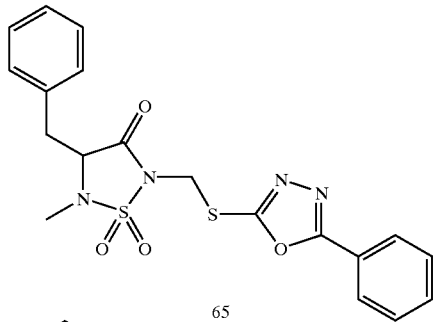
65
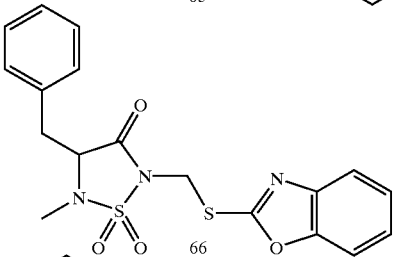
66
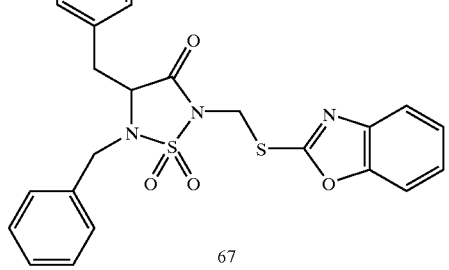
67
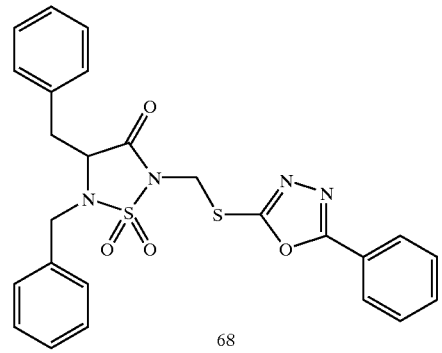
68
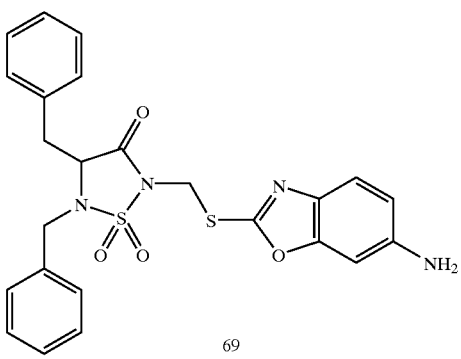
69

EXAMPLE 24

Sulfone Libraries of E-1

A sulfide library (0.75 mmol) in dry methylene chloride (4 mL) was treated with 70% m-chloroperbenzoic acid (2 mmol) and the solution stirred overnight at room temperature. Work up yielded the corresponding sulfone library (Table 1, 25–30).

III. Biological Activity

Protease Inhibition

An in vitro assay was used to screen compounds of the invention for the ability to reduce or inhibit serine protease activity. The human leukocyte elastase (HLE), cathepsin G (Cat G) and proteinase 3 (PR 3) assays have each been described in detail, Groutas et al. (1997) *Biochemistry* 36, 4739–4750. Chymase was assayed using N-succinyl Ala-Ala-Pro-Phe p-nitroanilide and 0.45 M Tris buffer/1.8 M NaCl, pH 8.03, Schechter, N. M. et al. (1993) *J. Biol. Chem.* 268, 23626–23633.

EXAMPLE 25

Figure 2:
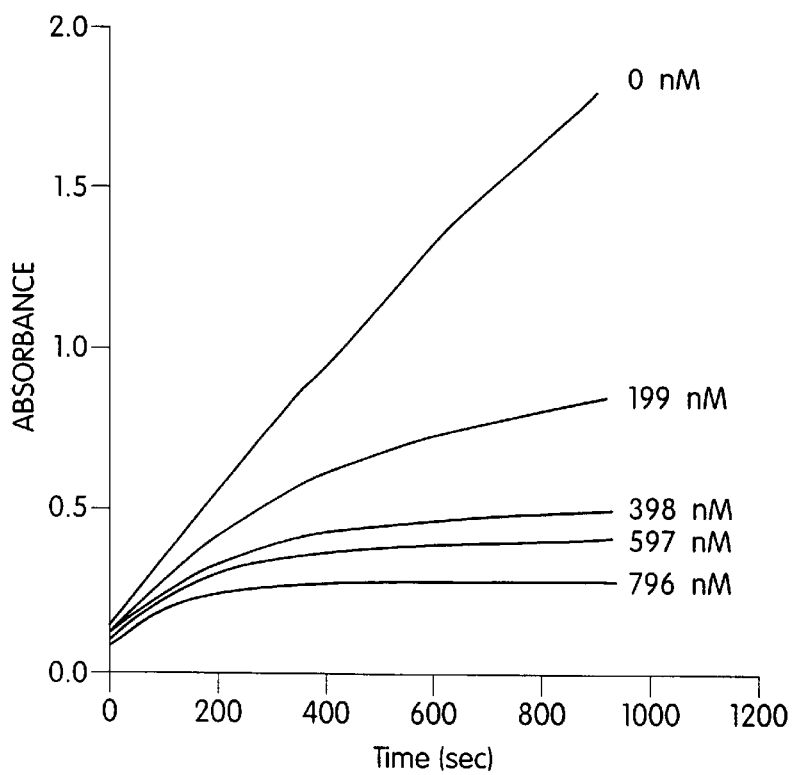
FIG. 2 shows an absorbance progress curve for the inhibition of human leukocyte elastase (HLE) by compound 53. (Table 4). Absorbance was monitored at 410 nm for reaction solutions containing 20.0 nM HLE, 1.00 mM MeOSuc-Ala-Ala-Pro-Val p-nitroanilide, and the indicated concentrations of inhibitor in 0.1 M HEPES buffer, pH 7.25, and 3.6% dimethyl sulfoxide. The temperature was maintained at 25° C., and the reactions were initiated by the addition of enzyme.

The rates of inactivation of HLE, Cat G or PR3 by each compound (or library of compounds) were determined by the progress curve method [Morrison, J. F. & Walsh, C. T. (1988) *Adv. Enzymol.* 61, 201–301]. Typical progress curves using a representative sulfonamide or heterocyclic sulfide inhibitor are illustrated in FIGS. 1 and 2, respectively. The apparent second-order rate constants $k_{inact}/k_I$ $M^{-1}$ $s^{-1}$, the magnitude of which serves as an index of inhibitory potency, were determined by the progress curve method and are listed in Table 5 (sulfonamides), Table 6 (heterocyclic sulfides), Table 3 (oxa acids), Tables 7 & 8 (libraries 1–30), and Table 9 (reversible inhibitors).

TABLE 5

Inhibitory Activity of Sulfonamides 31–49 Toward Human Leukocyte Elastase, Proteinase 3 and Cathepsin G

| | $k_{inact}/K_I$ $M^{-1}$ $s^{-1}$ | | |
|---|---|---|---|
| Compound | HLE | PR 3 | Cat G |
| 31 | 11,900 | — | — |
| 32 | 40,500 | — | — |
| 33 | 22,000 | — | — |
| 34 | 51,090 | — | — |
| 35 | 70,480 | — | — |
| 36 | — | — | 90 |
| 37 | — | — | 80 |
| 38 | 1,970 | — | 5,380 |
| 39 | 71,020 | — | — |
| 40 | 28,340 | 10,110 | 220 |
| 41 | 9,870 | — | — |
| 42 | 140,460 | 27,450 | — |
| 43 | 229,360 | 27,400 | 60 |
| 44 | 148,940 | — | — |
| 45 | 133,960 | 30,120 | 70 |
| 46 | 92,700 | 29,710 | inactive |
| 47 | inactive | — | — |
| 48 | 14,140 | 5,190 | 70 |
| 49 | 850 | — | — |

TABLE 6

Inhibitory Activity of Heterocyclic Sulfides 53–69 Toward Human Leukocyte Elastase, Proteinase 3 and Cathepsin G

| | $k_{inact}/K_I$ $M^{-1}$ $s^{-1}$ | | |
|---|---|---|---|
| Compound | HLE | PR 3 | Cat G |
| 53 | 153,460 | — | — |
| 54 | 67,300 | — | — |
| 55 | 174,440 | 9,130 | 60 |
| 56 | 560 | — | — |
| 57 | 80,580 | 10,350 | 30 |
| 58 | 168,130 | — | — |
| 59 | 22,360 | — | — |
| 60 | 1,540 | — | — |
| 61 | 25,280 | — | — |
| 62 | 67,840 | — | — |
| 63 | 22,630 | — | — |
| 64 | inactive | 1,090 | 50 |
| 65 | inactive | — | 490 |
| 66 | — | — | 430 |
| 67 | — | — | 17,130 |
| 68 | — | — | 17,460 |
| 69 | — | — | 15,740 |

TABLE 7

Inhibitory Activity of Libraries 1–30 Toward Human Leukocyte Elastase, Cathepsin G and Chymase

| | $k_{inact}/K_I$ $M^{-1}$ $s^{-1}$ | | |
|---|---|---|---|
| Library | HLE | Cat G | Chymase |
| 1 | 18,950 | 220 | — |
| 2 | 63,210 | 3,350 | — |
| 3 | 5,030 | 33,430 | 23,090 |
| 4 | 21,560 | 650 | — |
| 5 | 115,710 | 30,270 | 24,710 |
| 6 | 17,450 | 740 | — |
| 7 | 3,430 | 260 | inactive |
| 8 | 58,300 | 1,520 | inactive |
| 9 | — | 890 | 25,680 |
| 10 | — | 330 | — |
| 11 | 49,490 | 19,190 | 20,910 |
| 12 | 2,990 | 770 | 3,520 |
| 13 | — | 180 | inactive |
| 14 | 7,970 | 840 | inactive |
| 15 | — | 2,230 | 3,250 |
| 16 | — | 110 | — |
| 17 | 10,510 | 300 | 6,720 |
| 18 | — | 490 | — |
| 19 | — | inactive | inactive |
| 20 | — | — | inactive |
| 21 | — | inactive | — |
| 22 | — | inactive | inactive |
| 23 | — | — | inactive |
| 24 | — | — | inactive |
| 25 | — | inactive | inactive |
| 26 | 36,950 | 450 | inactive |
| 27 | — | 9,100 | — |
| 28 | — | inactive | inactive |
| 29 | 44,000 | 1,200 | — |
| 30 | — | inactive | inactive |

TABLE 8

Inhibitory Activity of Libraries 1, 7, 13 and 25 Toward Human Leukocyte Proteinase 3

| Library | $k_{inact}/K_I$ $M^{-1}$ $s^{-1}$ |
|---|---|
| 1 | 16,460 |
| 7 | 7,770 |

TABLE 8-continued

Inhibitory Activity of Libraries 1, 7, 13 and 25 Toward Human Leukocyte Proteinase 3

| Library | $k_{inact}/K_I$ $M^{-1}$ $s^{-1}$ |
|---|---|
| 13 | 4,550 |
| 25 | 4,440 |

TABLE 9

Inhibitory Activity of E-1g, E-1i, E-1j Toward Human Leukocyte Elastase

| Compound (library) | Inhibitory Activity |
|---|---|
| E-1g | $K_I$ 4.5 μM |
| E-1i | 46% inhibition |
| E-1j | 34% inhibition |

EXAMPLE 26

Figure 3:
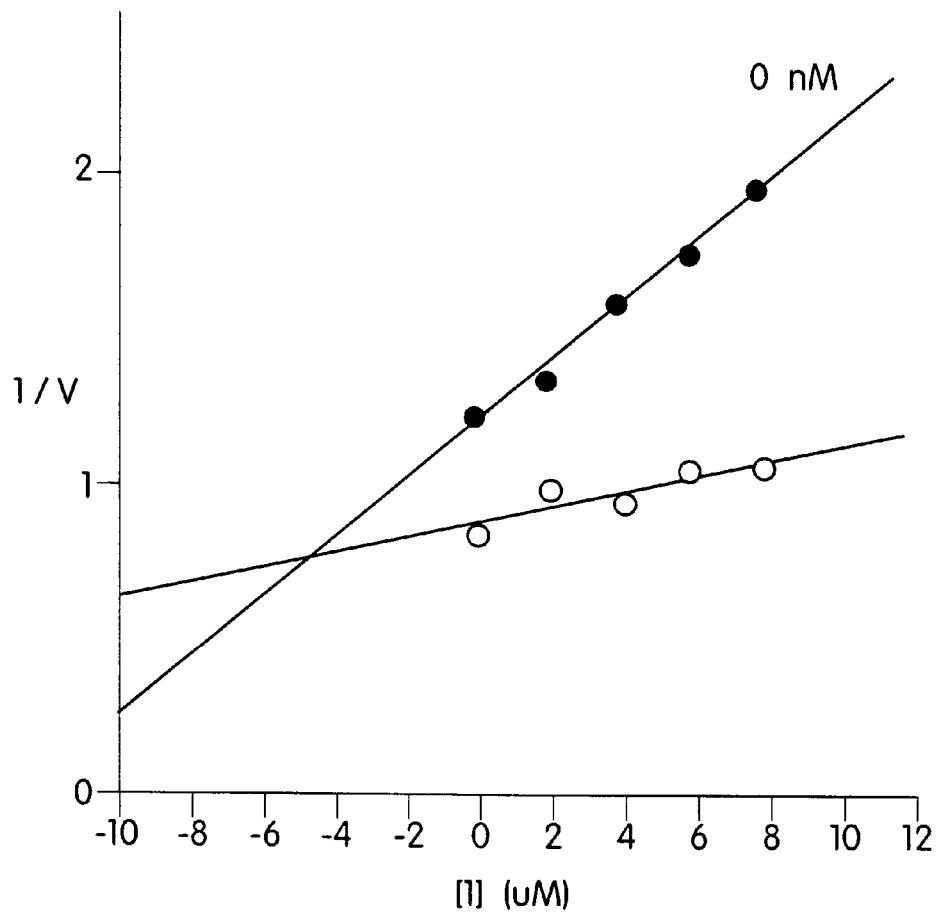
FIG. 3 shows a Dixon plot of inhibitor E-1 g and human leukocyte elastase. Human leukocyte elastase (20.8 nM) in 0.1 M HEPES buffer, pH 7.25, was added to a cuvette containing MeOSuc-Ala-Ala-Pro-Val p-nitroanilide (0.119 mM or 0.357 mM) and inhibitor E-1 g (0–8 μM) and the absorbance was monitored at 410 nm for 2 minutes at 25° C.

The inhibitory activity of compounds E-1 g through E-1i and library E-1j toward human leukocyte elastase was determined under competitive inhibition conditions. The $K_I$ value for compound E-1 g was determined using a Dixon plot [Dixon, M. (1953) *Biochem. J.* 55, 70–71] (FIG. 3 and Table 9).

EXAMPLE 27
Inhibition of α-chymotrypsin

Inhibition of α-Chymotrypsin was assayed using N-succinyl Ala-Ala-Pro-Phe p-nitroanilide and 0.1 M Tris buffer, pH 7.8, containing 0.1 M $CaCl_2$, DelMar, E. G. et al. (1979) *Analyt. Biochem.* 99, 316–320. Inhibition of bovine trypsin was assayed using N-α-benzoyl-L-Arg p-nitroanilide and 0.025 M phosphate buffer, pH 7.50, Kam, C-H. et al. (1994) *J. Med. Chem.* 37, 1298–1306. Inhibition of human granzyme B was assayed as described by Peisch, M. C. & Tschopp, J. (1994) *Meth. Enzymol.* 244, 80–87; Poe, M. et al. (1991) *J. Biol. Chem.* 266, 98–103.

The compounds or libraries of compounds represented by E-1 are screened to measure inhibitory activities in a panel of mammalian, viral and bacterial serine and cysteine proteases of clinical relevance such as, for example, mast cell tryptase [Delaria, K. et al. (1996) *Anal. Biochem.* 236, 74–81], human thrombin [Kam, C-H. et al. (1994) *J. Med. Chem.* 37, 1298–1306], hepatitis C virus protease [Bianchi, E. et al. (1996) *Analyt. Biochem.* 237, 239–244], human cytomegalovirus protease [Sardana, V. V. et al. (1994) *J. Biol. Chem.* 269, 14337–14340; Margosiak, S. A. et al. Biochemistry 35, 5300–5307], herpes simplex virus type 1 protease [DiIanni, C. L. et al. (1994) *J. Biol. Chem.* 269, 12672–12676], human rhinovirus 3C protease [Webber, S. E. et al. (1996) *J. Med. Chem.* 39, 5072–5082; Sham, H. L. et al. (1995) *J. Chem. Soc. Perkin Trans I,* 1081–1082], varicella-zoster virus protease, β-lactamase [Bulychev, A. et al. (1995) *J. Am. Chem. Soc.* 117, 5938–5943] and acetyl cholinesterase [Pirrung, M. C. & Chen, J. (1995) *J. Am. Chem. Soc.* 117, 1240–1245].

EXAMPLE 28
Compound K-1a

A solution of (L)-4,5-dibenzyl-1,2,5-thiadiazolidin-3-one 1,1 dioxide (0.5 g; 1.58 mmol) and ethyl α-bromofluoroacetate (0.44 g; 2.37 mmol) in dry dimethyl formamide (3 mL) was treated with 60% sodium hydride (63 mmol; 1.58 mmol). The reaction mixture was kept at 55° C. for 1 h using a water bath. The solvent was removed in vacuo and the product was dissolved in ethyl acetate (35 mL) and washed with water (3×10 mL), 5% sodium bicarbonate (2×10 mL) and dried over anhydrous sodium sulfate. Evaporation of the solvent yielded a crude product (0.56 g) which was purified by flash chromatography using silica gel and a hexane/methylene chloride gradient. The product K-1a (0.15 g; 25% yield) was screened against human leukocyte cathepsin G using the progress curve method ($k_{inact}/K_i$>10, 000 $M^{-1}$ $s^{-1}$).

Scheme 1

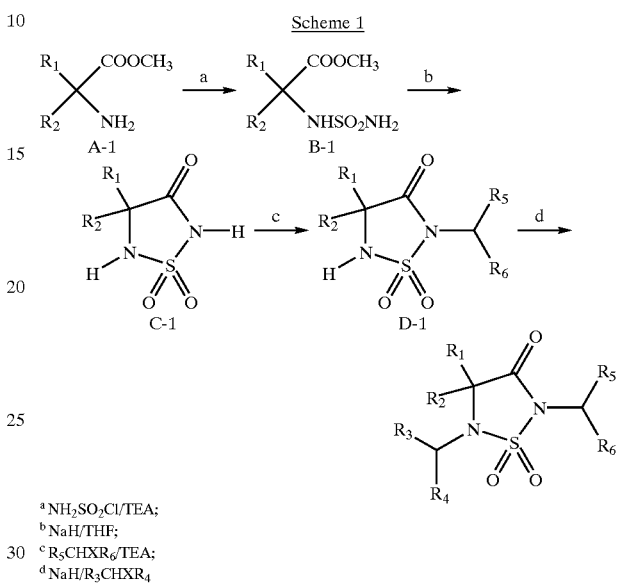

a $NH_2SO_2Cl/TEA$;
b $NaH/THF$;
c $R_5CHXR_6/TEA$;
d $NaH/R_3CHXR_4$

Scheme 2

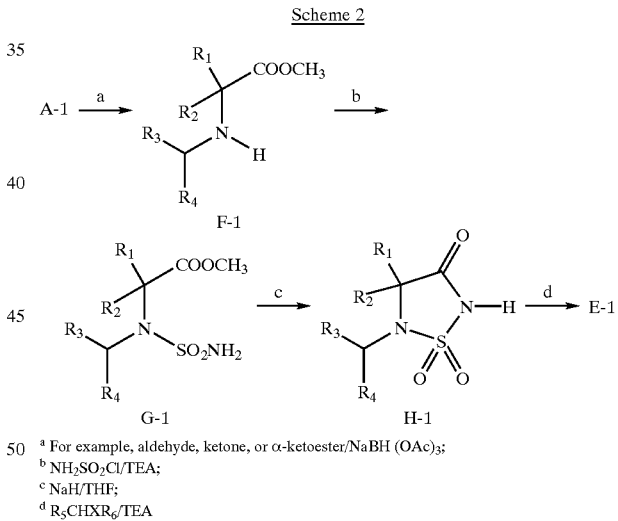

a For example, aldehyde, ketone, or α-ketoester/NaBH $(OAc)_3$;
b $NH_2SO_2Cl/TEA$;
c $NaH/THF$;
d $R_5CHXR_6/TEA$ Scheme 3

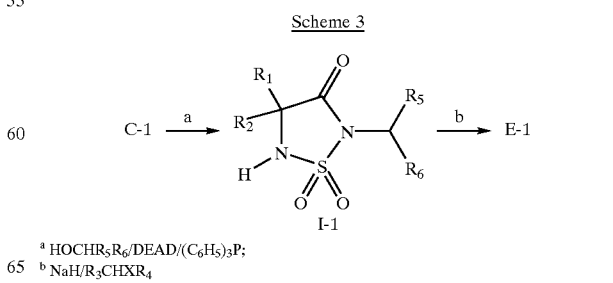

a $HOCHR_5R_6/DEAD/(C_6H_5)_3P$;
b $NaH/R_3CHXR_4$

Scheme 4

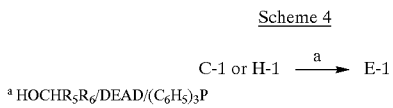

$^a$ HOCHR$_5$R$_6$/DEAD/(C$_6$H$_5$)$_3$P

Scheme 5

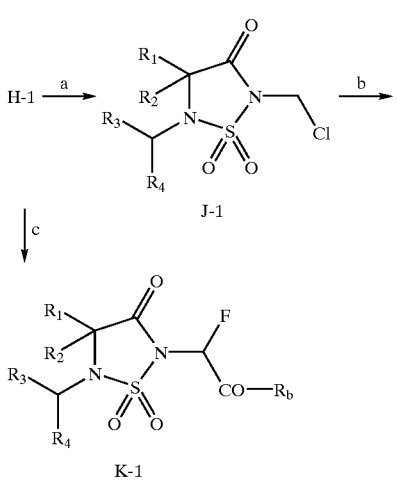

E-1 [where R$_6$ = leaving group, including HetS—, RCOO— and —N(SO$_2$R)COR]

$^a$HOSO$_3$Na/SOCl$_2$;
$^b$For example, 2-mercaptobenzoxazole/DBU, or NaI/acetone followed by 3, 6, 9-trioxodecanoic acid
$^c$BrCHFCOOEt/base

OTHER EMBODIMENTS

Based on the above description, one of ordinary skill in the art would easily discern the essential features of the invention and be able to adapt them to various usages and conditions without departing from the spirit and scope thereof.

What is claimed is:

1. A compound having the formula

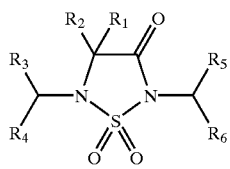

wherein, each of R$_1$, R$_3$ and R$_5$ is independently selected from H, alkyl, aryl, aralkyl, alkaryl and substituted aryl;

R$_2$ is selected from H, alkyl, aryl, aralkyl, alkylthioalkyl, acyloxyalkyl, alkyloxyalkyl, hydroxyalkyl, alkyl amine, alkyl thiol, alkyl alcohol and functional group having the formula alkyl —C(O)—;

R$_4$ and R$_6$ are each independently selected from the group consisting of H, alkyl, aryl, araalkyl, and a functional group having the formula —C(O)— where at least one of R$_4$ and R$_6$ has a functional group, having the formula —C(O)—.

2. The compound of claim 1, wherein R$_2$ has the formula

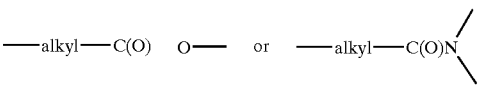

3. The compound of claim 1, wherein R$_4$ is a functional group having the formula

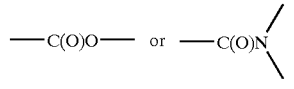

4. The compound of claim 3, wherein R$_6$ is a functional group having the formula

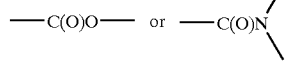

5. The compound of claim 1, wherein R$_4$ and R$_6$ are each independently a functional group having the formula

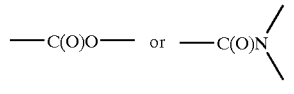

6. The compound of claim 1, wherein R$_4$ is selected from the group consisting of —COOH, —COOJ, and

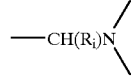

where R$_i$ is alkyl or aryl and J is a carboxylic acid protecting group.

7. The compound of claim 1, wherein R$_6$ is selected from the group consisting of —COOH, —COOJ,

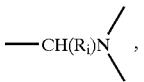

and —NHW where R$_i$ is alkyl or aryl, J is a carboxylic acid protecting group, and W is H, alkyl, aryl or an amino protecting group.

8. The compound of claim 1, wherein R$_2$ is selected from alkylacyloxyalkyl, and arylalkyloxyalkyl.

9. The compound of claim 1, wherein R$_1$ is selected from Val, Leu, Norval, Norleu, Abu, and Phe.

10. The compound of claim 1, wherein at least one of R$_3$ and R$_5$, is H.

11. The compound of claim 1, wherein R$_4$ is not H.

12. The compound of claim 1, wherein at least one of each pair selected from R$_1$, and R$_2$, R$_3$, and R$_4$, and R$_5$ and R$_6$, has a fragment formula weight of less than 150.

13. The compound of claim 1, wherein R$_4$ and R$_6$ are the same.

14. A method of for reducing or inhibiting the activity of a serine protease, comprising:

contacting a serine protease with a compound of the general formula

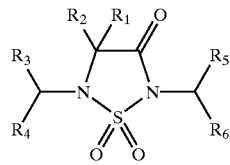

wherein,
  each of $R_1$, $R_3$ and $R_5$ is independently selected from H, alkyl, aryl, aralkyl, alkaryl and substituted aryl;
  $R_2$ is selected from H, alkyl, aryl, aralkyl, alkylthioalkyl, acyloxyakyl, alkyloxyalkyl, hydroxyalkyl, alkyl amine, alkyl thiol, alkyl alcohol and functional group having the formula alkyl —C(O)—;
  $R_4$ and $R_6$ are each independently selected from the group consisting of H, alky, araalkyl, and a functional group having the formula —C(O)— where at least one of $R_4$ and $R_6$ has a functional group having the formula —C(O)—.

15. The method of claim 14, wherein $R_2$ has the formula

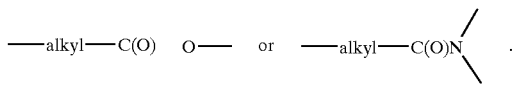

16. The method of claim 14, wherein $R_4$ is a functional group having the formula

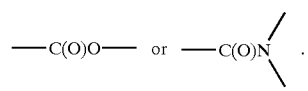

17. The method of claim 14, wherein $R_6$ is a functional group having the formula

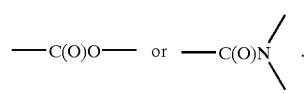

18. The method of claim 14, wherein $R_4$ and $R_6$ are each independently a functional group having the formula

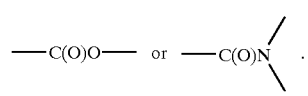

19. The method of claim 14, wherein $R_4$ is selected from the group consisting of —COOH, —COOJ, and

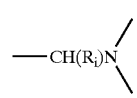

where $R_i$ is alkyl or aryl and J is a carboxylic acid protecting group.

20. The method of claim 14, wherein $R_6$ is selected from the group consisting of —COOH, —COOJ,

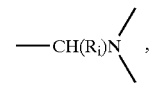

and —NHW where $R_i$ is alkyl or aryl, J is a carboxylic acid protecting group, and W is H, alkyl, aryl or an amino protecting group.

21. The method of claim 14, wherein $R_2$ is selected from alkylacyloxyalkyl, and arylalkyloxyalkyl.

22. The method of claim 14, wherein $R_i$ is selected from Val, Leu, Norval, Norleu, Abu, and Phe.

23. The method of claim 14 wherein at least one of $R_3$ and $R_5$, is H.

24. The method of claim 14, wherein $R_4$ is not H.

25. The method of claim 14, wherein at least one of each pair selected from $R_1$, and $R_2$, $R_3$, and $R_4$, and $R_5$ and $R_6$, has a fragment formula weight of less than 150.

26. The method of claim 14, wherein $R_4$ and $R_6$ are the same.

27. A compound having the formula

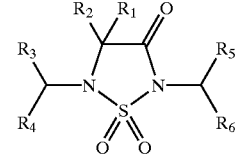

wherein,
  each of $R_1$, $R_3$ and $R_5$ is independently selected from H, alkyl, aryl, aralkyl, alkaryl and substituted aryl;
  $R_2$ is selected from H, alkyl, aryl, aralkyl, alkylthioalkyl, acyloxyalkyl, alkyloxyalkyl, hydroxyalkyl, alkyl amine, alkyl thiol, alkyl alcohol and functional group having the formula alkyl —C(O)—;
  $R_4$ is $(CHR_i)_m N{=}C{=}O$ or C(O)X, where X is a halide and m is 0 or 1; and
  $R_6$ is selected from the group consisting of H, alkyl, aryl, araalkyl, a functional group having the formula —C(O)—.

28. The compound of claim 27, wherein $R_2$ has the formula

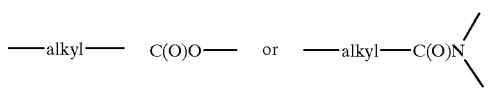

29. The compound of claim 27, wherein $R_4$ is N=C=O or C(O)X.

30. A compound having the formula

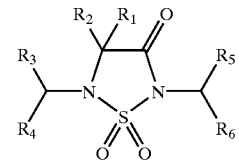

wherein,
  each of $R_1$, $R_3$ and $R_5$ is independently selected from H, alkyl, aryl, aralkyl, alkaryl and substituted aryl;
  $R_2$ is selected from H, alkyl, aryl, aralkyl, alkylthioalkyl, acyloxyalkyl, alkyloxyalkyl, hydroxyalkyl, alkyl amine, alkyl thiol, alkyl alcohol and functional group having the formula alkyl —C(O)—; and R$_4$ is selected from the group consisting of H, alkyl, aryl, araalkyl, and a functional group having the formula —C(O)—; and R$_6$ is (CHR$_i$)$_m$N=C=O or C(O)X, where X is a halide and m is 0 or 1.

31. The compound of claim 30, wherein R$_2$ has the formula

—alkyl— C(O)O—    or    —alkyl—C(O)N⟨

32. The compound of claim 30, wherein R$_6$ is N=C=O or C(O)X.

33. A compound having the formula wherein, each of R$_1$, R$_3$ and R$_5$ is independently selected from H, alkyl, aryl, aralkyl, alkaryl and substituted aryl;

R$_2$ is selected from a naturally occurring amino acid sidechain; and

R$_4$ and R$_6$ are each independently selected from the group consisting of H, alkyl, aryl, araalkyl, and a functional group having the formula —C(O)— where at least one of R$_4$ and R$_6$ has a functional group having the formula —C(O)—.

34. The compound of claim 33, wherein R$_6$ is a functional group having the formula —C(O)X where X is a halide and m is 0 or 1.

35. A compound having the formula wherein, each of R$_1$ and R$_3$ is independently selected from H, alkyl, aryl, aralkyl, alkaryl and substituted aryl;

R$_2$ is selected from H, alkyl, aryl, aralkyl, alkylthioalkyl, alkyloxyalkyl, hydroxyalkyl, alkyl amine, alkyl thiol, alkyl alcohol and functional group having the formula alkyl —C(O)—;

R$_4$ is selected from the group consisting of alkyl, aryl, araalkyl, and a functional group having the formula —C(O)—;

R$_5$ is independently selected from H, alkyl, aryl, aralkyl, alkaryl and substituted aryl; and R$_6$ is selected from the group consisting of alkyl, aryl, araalkyl, and a functional group having the formula —C(O)—.

36. A method of for reducing or inhibiting the activity of a serine protease, comprising:

contacting a serine protease with a compound of the general formula wherein, each of R$_1$ and R$_3$ is independently selected from H, alkyl, aryl, aralkyl, alkaryl and substituted aryl;

R$_2$ is selected from H, alkyl, aryl, aralkyl, alkylthioalkyl, acyloxyalkyl, alkyloxyalkyl, hydroxyalkyl, alkyl amine, alkyl thiol, alkyl alcohol and functional group having the formula alkyl —C(O)—;

R$_4$ is selected from the group consisting of alkyl, aryl, araalkyl, and a functional group having the formula —C(O)—;

R$_5$ is independently selected from H, alkyl, aryl, aralkyl, alkaryl and substituted aryl; and R$_6$ is selected from the group consisting of alkyl, aryl, araalkyl, and a functional group having the formula —C(O)—.

* * * * *

UNITED STATES PATENT AND TRADEMARK OFFICE
CERTIFICATE OF CORRECTION

PATENT NO. : 6,420,401 B1
DATED : July 16, 2002
INVENTOR(S) : William C. Groutas and Rongze Kuang It is certified that error appears in the above-identified patent and that said Letters Patent is hereby corrected as shown below:

<u>Title page,</u>
Item [56], OTHER PUBLICATIONS, replace "Groutas, W.C. et al., Structure-Based Design of Amino Acid-Derived Heterocyclic Mechanism-Based Inhibitors of Serine Proteinases, "A Abstract for Protease Inhibitors in Infectious Diseases" with -- Groutas, W.C. et al., "Structure-Based Design of Amino Acid-Derived Heterocyclic Mechanism-Based Inhibitors of Serine Proteinases," Abstract for "Protease Inhibitors in Infectious Diseases" --;

<u>Column 2,</u>
Line 19, replace "aand" with -- and --;

<u>Column 5,</u>
Line 38, replace "&" with -- $R_6$ --;

<u>Column 6,</u>
Line 52, replace "akyl" with -- alkyl --;

<u>Column 12,</u>
Line 25, replace "m/L" with -- mL --;

<u>Column 16,</u>
Line 16, replace "(t," with -- (t,1H) --;
Line 38, replace "3.91 4.18" with -- 3.91 (t,1H), 4.18 --;

<u>Column 29,</u>
Line 66, replace "at 55°C" with -- at ~55°C --;

UNITED STATES PATENT AND TRADEMARK OFFICE
CERTIFICATE OF CORRECTION

PATENT NO. : 6,420,401 B1
DATED : July 16, 2002
INVENTOR(S) : William C. Groutas and Rongze Kuang It is certified that error appears in the above-identified patent and that said Letters Patent is hereby corrected as shown below:

Column 33,
Line 14, replace "acyloxyakyl" with -- acyloxyalkyl --.

Signed and Sealed this

Fifth Day of August, 2003

JAMES E. ROGAN
*Director of the United States Patent and Trademark Office*